United States Patent [19]
Worton et al.

[11] Patent Number: 5,413,907
[45] Date of Patent: May 9, 1995

[54] DIAGNOSIS FOR MALIGNANT HYPERTHERMIA

[75] Inventors: Ronald G. Worton; David H. MacLennan, both of Toronto; Beverley A. Britt, Etobicoke, all of Canada

[73] Assignees: The University of Toronto Innovations Foundation; HSC Research and Development Limited Partnership; The Toronto Hospital, all of Toronto, Canada

[21] Appl. No.: 842,396
[22] PCT Filed: Sep. 21, 1990
[86] PCT No.: PCT/CA90/00312
  § 371 Date: Apr. 13, 1992
  § 102(e) Date: Apr. 13, 1992
[87] PCT Pub. No.: WO91/04328
  PCT Pub. Date: Apr. 4, 1991

[30] Foreign Application Priority Data
  Sep. 25, 1989 [CA] Canada .................. 612726

[51] Int. Cl.$^6$ .......... C12Q 1/68; C07H 21/04
[52] U.S. Cl. .......... 435/6; 536/23.5; 536/24.31
[58] Field of Search .......... 435/6, 320.1, 240.2; 536/27

[56] References Cited

U.S. PATENT DOCUMENTS 4,837,163 6/1989 Ohnishi .................. 436/63

OTHER PUBLICATIONS

"Primary Structure And Expression From Complementary DNA Of Skeletal Muscle Ryanodine Receptor"; by Takeshima et al; vol. 339; pp. 439–445.
"Molecular Cloning of cDNA Encoding Human And Rabbit Forms Of The $Ca^{2+}$ Release Channel (Ryanodine Receptor) Of Skeletal Muscle Sarcoplasmic Reticulum*"; By Zorzato, et al; pp. 2244–2256; vol. 265, No. 4 Issue of Feb. 5, 1990 of The Journal Of Biological Chemistry.
"Chemical Abstracts"; By Chemical Abstracts Service; vol. 107; No. 1; Jul. 6, 1987.
"Structural And Functional Correlation Of The Trypsin-digested $Ca^{2+}$ Release Channel Of Skeletal Muscle Sarcoplasmic Retinulum*"; by Meissner, et al; pp. 1715–1722; The Journal of Biological Chemistry.
Oding, H., (1985) Incidence of Malignant Hyperthermia in Denmark, Anesth Analg 64:700–704.
Rosenger, H. et al, (1986) Masseter Muscle Rigidity and Malignant Hyperthermia Susceptibility.
Kalow, W. Inheritance of Malignant Hyperthermia–A Review of Published Data, In Britt, B. A., Ed. Mal. Hyp. Boston Martinus Nijhoff pp. 155–180 1987.
Britt, B. A., Preface: A History of Malignant Hyper- (List continued on next page.)

Primary Examiner—Margaret Parr
Assistant Examiner—Kenneth Horlick
Attorney, Agent, or Firm—Bell, Seltzer, Park & Gibson

[57] ABSTRACT

A method for isolating a cDNA specific for the human ryanodine receptor is disclosed. The gene is associated with malignant hyperthermia, a hypermetabolic syndrome triggered primarily by inhalation anesthetics. The cDNA can be cloned and expressed in a recombinant plasmid or phage. The cDNA, or fragments thereof, is used as diagnostic probes for individuals at risk for malignant hyperthermia using restriction fragment length polymorphism analysis. The cDNA is that sequenced in FIG. 2 of this specification.

4 Claims, 41 Drawing Sheets

OTHER PUBLICATIONS thermia in Britt, B. A., Ed. Mal. Hyp. Boston Martinus Nijhoff pp. 155–180 1987.

Steward, D. J. et al., Malignant Hyperthermia–The Acute Crisis in Britt, B. A. ed. Mal. Hyp. Boston Martinus Nijhoff pp. 1–10 1987.

Kalow, W. et al, (1970) Metabolic Error of Muscle Metabolism After Recovery from Malignant Hyperthermia, Lancet 2:895–898.

Britt, B. A., Malignant Hyperthermia–Pattern of Inheritance in Swine in Aldrete, J. A. ed., Second International Symposium on Malignant Hyperthermia, New York, Crune and Stratton pp. 195–211 (1978).

Archibald, A. L. et al, (1985) The Halothane Sensitivity Locus and Its Linkage Relationships, Animal Blood Groups and Biochemical Genetics 16:253–263.

Shaw, Duncan, et al, Report of the Committee for Chromosomes 17, 18 and 19. Human Gene Mapping 9 (1987) Ninth International Workshop on Human Gene Mapping Cytogenetics and Cell Genetics, vol. 46 Nos. 1–4 (1987).

Botstein, D. et al, (1980) Construction of a Genetic Linkage Map in Man Using Restriction Fragment Length Polymorphisms Am. J. Hum. Genet. 32:314–331.

Mickelson et al., *J. Biol. Chem.* 263(19), 9310–9315 (1988).

FIG. 2A.

```
GTCTCCGAGG  TCTCCGACCC  CGCCCGCGCC  CAGCCCTCCC  GCCCAGCCCG    50

CAGCCCCCTC  CCTCTGTTCC  CCGACCTCAG  ACCCTGGGCT  TCCGACCTCG   100

ACATCATGGG  TGACGCAGAA  GGCGAAGACG  AGGTCCAGTT  CCTGCGACG    150
            MetGl       yAspAlaGlu  GlyGluAspG  luValGlnPh   eLeuArgThr

GACGATGAGG  TGGTCCTGCA  GTGCAGCGCT  ACCGTGCTCA  AGGAGCAGCT   200
AspAspGluV  alValLeuGl  nCysSerAla  ThrValLeuL  ysGluGlnLe

CAAGCTCTGC  CTGGCCGCCG  AGGGCTTCGG  CAACCGCCTG  TGCTTCCTGG   250
uLysLeuCys  LeuAlaAlaG  luGlyPheGl  yAsnArgLeu  CysPheLeuG

AGCCCCACTAG CAACGCGCAG  AATGTGCCCC  CCGATCTGGC  CATCTGTTGC   300
luProThrSe  rAsnAlaGln  AsnValProP  roAspLeuAl  aIleCysCys

TTCGTCCTGG  AGCAGTCCCT  GTCTGTGCGA  GCCCTGCAGG  AGATGCTGGC   350
PheValLeuG  luGlnSerLe  uSerValArg  AlaLeuGlnG  luMetLeuAl

TAACACGGTG  GAGGCTGGCG  TGGAGTCATC  CCAGGGCGGG  GGACACAGGA   400
aAsnThrVal  GluAlaGlyV  alGluSerSe  rGlnGlyGly  GlyHisArgT

CGCTCCTGTA  TGGCCATGCC  ATCCTGCTCC  GGCATGCACA  CAGCCGCATG   450
hrLeuLeuTy  rGlyHisAla  IleLeuLeuA  rgHisAlaHi  sSerArgMet
```

FIG. 2B.

```
TATCTGAGCT GCCTCACCAC CTCCCGCTCC ATGACTGACA AGCTGGCCTT  500
TyrLeuSerC ysLeuThrTh rSerArgSer MetThrAspL ysLeuAlaPh

CGATGTGGGA CTGCAGGAGG ACGCAACAGG AGAGGCTTGC TGGTGGACCA  550
eAspValGly LeuGlnGluA spAlaThrGl yGluAlaCys TrpTrpThrM

TGCACCCAGC CTCCAAGCAG AGGTCTGAAG GAGAAAAGGT CCGCGTTGGG  600
etHisProAl aSerLysGln ArgSerGluG lyGluLysVa lArgValGly

GATGACATCA TCCTTGTCAG TGTCTCCTCC GAGCGCTACC TGCACCTGTC  650
AspAspIleI leLeuValSe rValSerSer GluArgTyrL euHisLeuSe

GACCGCCAGT GGGGAGCTCC AGGTTGACGC TTCCTTCATG CAGACACTGT  700
rThrAlaSer GlyGluLeuG lnValAspAl aSerPheMet GlnThrLeuT

GGAACATGAA CCCCATCTGC TCCCGCTGCG AAGAGGGCTT CGTGACGGGA  750
rpAsnMetAs nProIleCys SerArgCysG luGluGlyPh eValThrGly

GGTCACGTCC TCCGCCTCTT TCATGGACAT ATGGATGAGT GTCTGACCAT  800
GlyHisVall euArgLeuPh eHisGlyHis MetAspGluC ysLeuThrIl TTCCCCTGCT GACAGTGATG ACCAGCGCAG ACTTGTCTAC TATGAGGGGG  850
eSerProAla AspSerAspA spGlnArgAr gLeuValTyr TyrGluGlyG GAGCTGTGTG CACTCATGCC CGCTCCCTCT GGAGGCTGGA GCCACTGAGA  900
lyAlaValCy sThrHisAla ArgSerLeuT rpArgLeuLeu ProLeuArg
```

FIG.2C.

```
ATCAGCTGGA GTGGGAGCCA CCTGCGCTGG GGCCAGCCAC TCCGAGTCCG    950
IleSerTrpS erGlySerHi sLeuArgTrp GlyGlnProL euArgValAr

GCATGTCACT ACCGGGCAGT ACCTAGCGCT CACCGAGGAC CAGGGCCTGG   1000
gHisValThr ThrGlyGlnT yrLeuAlaLe uThrGluAsp GlnGlyLeuV

TGGTGGTTGA CGCCAGCAAG GCTCACACCA AGGCTACCTC CTTCTGCTTC   1050
alValValAs pAlaSerLys AlaHisThrL ysAlaThrSe rPheCysPhe

CGCATCTCCA AGGAGAAGCT GGATGTGGCC CCCAAGCGGG ATGTGGAGGG   1100
ArgIleSerL ysGluLysLe uAspValAla ProLysArgA spValGluGl

CATGGGCCCC CCTGAGATCA AGTACGGGGA GTCACTGTGC TTCGTGCAGC   1150
yMetGlyPro ProGluIleL ysTyrGlyGl uSerLeuCys PheValGlnH

ATGTGGCCTC AGGACTGTGG CTCACCTATG GAAGAAGGCC CCGCTCCAGA   1200
isValAlaSe rGlyLeuTrp LeuThrTyrA laLysLysAla pProLysAla

CTGCGGCTCG GCGTGCTCAA GCGTGCTCAA ATGCTGCACC AGGAGGGCCA   1250
LeuArgLeuG lyValLeuLy sLysLysAla MetLeuHisG lnGluGlyHi

CATGGACGAC GCACTGTCGC TGACCCGCTG CCAGCAGGAG GAGTCCCAGG   1300
sMetAspAsp AlaLeuSerL euThrArgCy sGlnGlnGlu GluSerGlnA
```

FIG. 2D.

```
CCGCCCGCAT GATCCACAGC ACCAATGGCC TATACAACCA GTTCATCAAG  1350
laAlaArgMe tIleHisSer ThrAsnGlyL euTyrAsnGl nPheIleLys

AGCCTGGACA GCTTCAGCGG GAAGCCACGG GGCTCGGGGC CACCCGCTGG  1400
SerLeuAspS erPheSerGl yLysProArg GlySerGlyP roProAlaGl

CACGGCGCTG CCCATCGAGG GCGTTATCCT GAGCCTGCAG GACCTCATCA  1450
yThrAlaLeu ProIleGluG lyValIleLe uSerLeuGln AspLeuIleI

TCTACTTCGA GCCTCCCTCC GAGGACTTGC AGCACGAGGA GAAGCAGAGC  1500
leTyrPheGl uProProSer GluAspLeuG lnHisGluGl uLysGlnSer

AAGCTGCGAA GCCTGCGCAA CCGCCAGAGC CTCTTCCAGG AGGAGGGGAT  1550
LysLeuArgS erLeuArgAs nArgGlnSer LeuPheGlnG luGluGlyMe

GCTCTCCATG GTCCTGAATT GCATAGACCG TACACCACTG CCTAAATGTC  1600
tLeuSerMet ValLeuAsnC ysIleAspAr gTyrThrThrA gLeuAsnVal

CTGCCCACTT TGCTGAGTTT GCAGGGGAGG AGGCAGCCGA GTCCTGGAAA  1650
laAlaHisPh eAlaGluPhe AlaGlyGluG luAlaAlaGl uSerTrpLys

GAGATTGTGA ATCTTCTCTA TGAACTCCTA GCTTCTCTAA TCCGTGGCAA  1700
GluIleValA snLeuLeuTy rGluLeuLeu AlaSerLeuI leArgGlyAs
```

FIG.2E.

```
TCGTAGCAAC TGTGCCCTCT TCTCCACAAA CTTGGACTGG CTGGTCAGCA   1750
nArgSerAsn CysAlaLeuP heSerThrAs nLeuAspTrp LeuValSerL

AGCTGGATCG GCTGGAGGCC TCATCTGGCA TCCTGGAGGT CCTGTACTGT   1800
ysLeuAspAr gLeuGluAla SerSerGlyI leLeuGluVa lLeuTyrCys

GTCCTCATTG AGAGTCCAGA GGTTCTGAAC ATCATCCAGG AGAATCACAT   1850
ValLeuIleG luSerProGl uValLeuAsn IleIleGlnG luAsnHisIl

CAAGTCCATC ATCTCCCTCC TGGACAAGCA CACAAGGTCC              1900
eLysSerIle IleSerLeuL euAspLysHi sGlyArgAsn

TGGACGTGCT ATGCTCCCTG TGTGTGTGTA ATGGTGTGGC TGTACGCTCC   1950
euAspValLe uCysSerLeu CysValCysA snGlyValAl aValArgSer

AACCAAGATC TTATTACTGA GAACTTGCTG CCTGGCCGTG AGCTTCTGCT   2000
AsnGlnAspL euIleThrGl uAsnLeuLeu ProGlyArgG luLeuLeuLe

GCAGACAAAC CTCATCAACT ATGTCACCAG CATCCGCCCC AACATCTTTG   2050
uGlnThrAsn LeuIleAsnT yrValThrSe rIleArgPro AsnIlePheV

TGGGCCGAGC GGAAGGCACC ACGCAGTACA GCAAATGGTA CTTTGAGGTG   2100
alGlyArgAl aGluGlyThr ThrGlnTyrS erLysTrpTy rPheGluVal
```

FIG. 2F.

```
ATGGTGGACG AGGTGACTCC ATTTCTGACA GCTCAGGCCA CCCACTTGCG  2150
MetValAspG luValThrPr oPheLeuThr AlaGlnAlaT hrHisLeuAr

GGTGGGCTGG GCCCTCACCG AGGGCTACAC CCCCTACCCT GGGGCCGGCG  2200
gValGlyTrp AlaLeuThrG luGlyTyrTh rProTyrPro GlyAlaGlyG

AGGGCTGGGG CGGCAACGGG GTCGGGCGATG ACCTCTATTC CTACGGCTTT  2250
luGlyTrpGl yGlyAsnGly ValGlyAspA spLeuTyrSe rTyrGlyPhe

GATGGACTGC ATCTCTGGAC AGGACACGTG GCACGCCCAG TGACTTCCCC  2300
AspGlyLeuH isLeuTrpTh rGlyHisVal AlaArgProV alThrSerPr

AGGGCAGCAC CTCCTGGCCC CTGAAGACGT GATCAGCTGC TGCCTGGACC  2350
oGlyGlnHis LeuLeuAlaP roGluAspVa lIleSerCys CysLeuAspL

TCAGCGTGCC GTCCATCTCC TTCCGCATCA ACGGCTGCCC TGTGCAGGGT  2400
euSerValPr oSerIleSer PheArgIleA snGlyCysPr oValGlnGly

GTCTTTGAGT CCTTCAACCT GGACGGGCTC TTCTTCCCTG TTGTCAGCTT  2450
ValPheGluS erPheAsnLe uAspGlyLeu PhePheProV alValSerPh

CTCGGCTGGT GTCAAGGTGC GGTTCCTCCT GGGTGGCCGC CATGGTGAAT  2500
eSerAlaGly ValLysValA rgPheLeuLe uGlyGlyArg HisGlyGluP
```

FIG. 2G.

```
TCAAGTTCCT GCCCCCACCT GGCTATGCTC CATGCCATGA GGCTGTGCTC 2550
heLysPheLe uProProPro GlyTyrAlaP roCysHisGl uAlaValLeu

CCTCGAGAGC GACTCCATCT TGAACCCATC AAGGAGTATC GACGGGAGGG 2600
ProArgGluA rgLeuHisLe uGluProIle LysGluTyrA rgArgGluGl

GCCCCGGGGG CCTCACCTGG TGGGCCCCAG TCGCTGCCTC TCACACACCG 2650
yProArgGly ProHisLeuV alGlyProSe rArgCysLeu SerHisThrA

ACTTCGTGCC CTGCCCTGTG GACACTGTCC AGATTGTCCT GCCGCCCCAT 2700
spPheValPr oCysProVal AspThrValG lnIleValLe uProProHis

CTGGAGCGCA TTCGGGAGAA GCTGGGCGAG AACATCCACG AGCTCTGGGC 2750
LeuGluArgI leArgGluLy sLeuAlaGlu AsnIleHisG luLeuTrpAl

GCTAACCCGC ATCGAGCAGG GCTGGACCTA CGGCCCGGTT CGGGATGACA 2800
aLeuThrArg IleGluGlnG lyTrpThrTy rGlyProVal ArgAspAspA

ACAAGAGGCT GCACCCGTGT CTTGTGGACT TCCACAGCCT TCCAGAGCCT 2850
snLysArgLe uHisProCys LeuValAspP heHisSerLe uProGluPro

GAGAGGAACT ACAACCTGCA GATGTCTGGG GAGACGCTCA AGACTCTGCT 2900
GluArgAsnT yrAsnLeuGl nMetSerGly GluThrLeuL ysThrLeuLe
```

FIG.2H.

```
GGCTCTGGGC TGCCACGTGG GCATGGCGGA TGAGAAGGCG GAGGACAACC 2950
uAlaLeuGly CysHisValG lyMetAlaAs pGluLysAla GluAspAsnL

TGAAGAAGAC AAAACTCCCC AAGACGTATA TGATGAGCAA TGGGTACAAG 3000
euLysLysTh rLysLeuPro LysThrTyrM etMetSerAs nGlyTyrLys

CCGGCTCCGC TGGACCTGAG CCACGTGCCG CTGACGCCGG CGCAGACAAC 3050
ProAlaProL euAspLeuSe rHisValArg LeuThrProA laGlnThrTh

ACTGGTGGAC CGTCTGGCAG AAAATGGGCA CAACGTGTGG GCCCGAGACC 3100
rLeuValAsp ArgLeuAlaG luAsnGlyHi sAsnValTrp AlaArgAspA

GCGTGGGCCA GGGCTGGAGC TACAGCGCAG TGCAGGACAT CCCAGGCCGC 3150
rgValGlyGl nGlyTrpSer TyrSerAlaV alGlnAspIl eProAlaArg

CGAAACCCTC GGCTGGTGCC CTACCGCCTG CTGGATGAAG CCACCAAGCG 3200
ArgAsnProA rgLeuValPr oTyrArgLeu LeuAspGluA laThrLysAr

CAGCAACCGG GACAGCCTCT GCCAGGCCGT GCGCACCCTC CTGGGCTACG 3250
gSerAsnArg AspSerLeuC ysGlnAlaVa lArgThrLeu LeuGlyTyrG

GCTACAACAT CGAGCCTCCT GACCAGGAGC CCAGTCAGGT GGAGAACCAG 3300
lyTyrAsnIl eGluProPro AspGlnGluP roSerGlnVa lGluAsnGln
```

FIG.21.

```
TCTCGTTGTG ACCGGGTGCG CATCTTCCGG GCAGAGAAAT CCTATACAGT   3350
SerArgCysA spArgValAr gIlePheArg AlaGluLysS erTyrThrVa

GCAGAGCGGC CGCTGGTACT TCGAGTTTGA AGCAGTCACC ACAGGCGAGA   3400
lGlnSerGly ArgTrpTyrP heGluPheGl uAlaValThr ThrGlyGluM

TGCGCGTGGG CTGGGCGAGG CCCGAGCTGA GGCCTGATGT AGAGCTGGGA   3450
etArgValGl yTrpAlaArg ProGluLeuA rgProAspVa lGluLeuGly

GCTGACGAGC TGGCCTATGT CTTCAATGGG CACCGCGGCC AGCGCTGGCA   3500
AlaAspGluL euAlaTyrVa lPheAsnGly HisArgGlyG lnArgTrpHi

CTTGGGCAGT GAACCATTTG GGCGCCCCTG GCAGCCGGGC GATGTCGTTG   3550
sLeuGlySer GluProPheG lyArgProTr pGlnProGly AspValValG

GCTGTATGAT CGACCTCACA GAGAACACCA TTATCTTCAC CCTCAATGGC   3600
lyCysMetIl eAspLeuThr GluAsnThrI leIlePheTh rLeuAsnGly

GAGGTCCTCA TGTCTGACTC AGGCTCCGAA ACAGCCTTCC GGGAGATTGA   3650
GluValLeuM etSerAspSe rGlySerGlu ThrAlaPheA rgGluIleG

GATTGGGGAC GGCTTCCTGC CCGTCTGCAG CTTGGGACCT GGCCAGGTGG   3700
uIleGlyAsp GlyPheLeuP roValCysSe rLeuGlyPro GlyGlnValG
```

FIG. 2J.

```
GTCATCTGAA CCTGGGCCAG GACGTGAGCT CTCTGAGGTT CTTTGCCATC 3750
lyHisLeuAs nLeuGlyGln AspValSerS erLeuArgPh ePheAlaIle

TGTGGCCTCC AGGAAGGCTT CGAGCCATTT GCCATCAACA TGCAGCGCCC 3800
CysGlyLeuG lnGluGlyPh eGluProPhe AlaIleAsnM etGlnArgPr

AGTCACCACC TGGTTCAGCA AAGGCCTGCC CCAGTTTGAG CCAGTGCCCC 3850
oValThrThr TrpPheSerL ysGlyLeuPr oGlnPheGlu ProValProL

TTGAACACCC TCACTATGAG GTATCCCGAG TGGACGGCAC TGTGGACACG 3900
euGluHisPr oHisTyrGlu ValSerArgV alAspGlyTh rValAspThr

CCCCCCTGCC TGCGCCTGAC CCACCGCACC TGGGGCTCCC AGAACAGCCT 3950
ProProCysL euArgLeuTh rHisArgThr TrpGlySerG lnAsnSerLe

GGTGGAGATG CTTTTCCTGC GGCTGAGCCT CCCAGTCCAG TTCCACCAGC 4000
uValGluMet LeuPheLeuA rgLeuSerLe uProValGln PheHisGlnH

ACTTCCGCTG CACTGCAGGG GCCACCCCGC TGGCACCTCC TGGCCTGCAG 4050
isPheArgCy sThrAlaGly AlaThrProL euAlaProPr oGlyLeuGln

CCCCCCGCCG AGGACGAGGC CCGGGGGGCG GAACCCGACC CTGACTACGA 4100
ProProAlaG luAspGluAl aArgAlaAla GluProAspP roAspTyrGl
```

FIG. 2K.

```
AAACCTGCGC CGCTCAGCTG GGGGCTGGAG CGAGGCAGAG AACGGCAAAG   4150
uAsnLeuArg ArgSerAlaG lyGlyTrpSe rGluAlaGlu AsnGlyLysG

AAGGGACTGC GAAGGAGGGC GCCCCCGGGG GCACCCCGCA GGCGGGGAGA   4200
luGlyThrAl aLysGluGly AlaProGlyG lyThrProGl nAlaGlyArg

GGCGCACCGG CCAGGGCGGA GAATGAGAAG GATGCCACCA CCGAGAAGAA   4250
GlyAlaProA laArgAlaGl uAsnGluLys AspAlaThrT hrGluLysAs

CAAGAAGAGA GGCTTCTTAT TCAAGGCCAA GAAGGTCGCC ATGATGACCC   4300
nLysLysArg GlyPheLeuP heLysAlaLy sLysValAla MetMetThrG

AGCCACCGGC CACCCCCACG CTGCCCCGAC TCCCTCACGA CGTGGTGCCT   4350
lnProProAl aThrProThr LeuProArgL euProHisAs pValValPro

GCAGACAACC GCGATGACCC CGAGATCATC CTCAACACCA CCACGTACTA   4400
AlaAspAsnA rgAspAspPr oGluIleIle LeuAsnThrT hrThrTyrTy

TTACTCCGTG AGGGTCTTTG CTGGACAGGA GCCCAGCTGC GTGTGGGCGG   4450
rTyrSerVal ArgValPheA laGlyGlnGl uProSerCys ValTrpAlaG

GCTGGGTCAC CCCTGACTAC CATCAGCACG ACATGAGCTT CGACCTCAGC   4500
lyTrpValTh rProAspTyr HisGlnHisA spMetSerPh eAspLeuSer
```

FIG.2L.

```
AAGGTCCGGG TCGTGACGGT GACCATGGGG GATGAACAAG GCAACGTCCA  4550
LysValArgV alValThrVa lThrMetGly AspGluGlnG lyAsnValHi

CAGCAGCCTC AAGTGTAGCA ACTGCTACAT GGTGTGGGGC GGAGACTTTG  4600
sSerSerLeu LysCysSerA snCysTyrMe tValTrpGly GlyAspPheV

TGAGTCCCGG GCAGCAGGGC CGGATCAGCC ACACGGACCT TGTCATTGGG  4650
alSerProGl yGlnGlnGly ArgIleSerH isThrAspLe uValIleGly

TGCCTGGTGG ACTTGGCCAC TGGCTTAATG ACCTTTACAG CCAATGGCAA  4700
CysLeuValA spLeuAlaTh rGlyLeuMet ThrPheThrA laAsnGlyLy

AGAGAGCAAC ACCTTTTTCC AGGTGGAACC CAACACTAAG CTATTTCCTG  4750
sGluSerAsn ThrPhePheG lnValGluPr oAsnThrLys LeuPheProA

CCGTCTTCGT CCTGCCCACC CACCAGAACG TCATCCAGTT TGAGCTGGGG  4800
laValPheVa lLeuProThr HisGlnAsnV alIleGlnPh eGluLeuGly

AAGCAGAAGA ACATCATGCC GTTGTCAGCC GCCATGTTCC AAAGGAGCCG  4850
LysGlnLysA snIleMetPr oLeuSerAla AlaMetPheG lnSerGluAr

CAAGAACCCG GCCCCGCAGT GCCCACCGCG GCTGGAGATG CAGATGCTGA  4900
gLysAsnPro AlaProGlnC ysProProAr gLeuGluMet GlnMetLeuM
```

FIG.2M.

```
TGCCAGTGTC CTGGAGCCGC ATGCCCAACC ACTTCCTGCA GGTGGAGACG   4950
etProValSe rTrpSerArg MetProAsnH isPheLeuGl nValGluThr

AGGCGTGCCG GCCAGCGGGCT GGGCTGGGCC GTGCAGTGCC AGGAGCCGCT   5000
ArgArgAlaG lyGluArgLe uGlyTrpAla ValGlnCysG lnGluProLe

GACCATGATG GCGCTGCACA TCCCCGAGGA GAACCGGTGC ATGGACATCC   5050
uThrMetMet AlaLeuHisI leProGluGl uAsnArgCys MetAspIleL

TGGAGCTGTC GGAGCGCCTG GACCTGCAGC GCTTCCACTC GCACACCCTG   5100
euGluLeuSe rGluArgLeu AspLeuGlnA rgPheHisSe rHisThrLeu

CGCCTCTACC GCGCTGTGTG CGCCCCTGGGC AACAATCGCG TGGCGCACGC   5150
ArgLeuTyrA rgAlaValCy sAlaLeuGly AsnAsnArgV alAlaHisAl

TCTGTGCAGC CACGTAGACC AAGCTCAGCT GCTGCACGCC CTGGAGGACG   5200
aLeuCysSer HisValAspG lnAlaGlnLe uLeuHisAla LeuGluAspA

CGCACCTGCC AGGCCCACTG CGCGCAGGCT ACTATGACCT CCTCATCAGC   5250
laHisLeuPr oGlyProLeu ArgAlaGlyT yrTyrAspLe uLeuIleSer

ATCCACCTCG AAAGTGCCTG CCGCAGCCGC CGCTCCATGC TCTCTGAATA   5300
IleHisLeuG luSerAlaCy sArgSerArg ArgSerMetL euSerGluTy
```

FIG. 2N.

```
CATCGTGCCC CTCACGCCTG AGACCCGCGC CATCACGCTC TTCCCTCCTG    5350
rIleValPro LeuThrProG luThrArgAl aIleThrLeu PheProProG

GAAGGAGCAC AGAAAATGGT CACCCCCGGC ATGGCCTGCC GGGAGTTGGA    5400
lyArgSerTh rGluAsnGly HisProArgH isGlyLeuPr oGlyValGly

GTCACCACTT CGCTGAGGCC CCCGCATCAT TTCTCGCCCC CCTGTTTCGT    5450
ValThrThrS erLeuArgPr oProHisHis PheSerProP roCysPheVa

GGCCGCTCTG CCAGCTGCTG GGGCAGCAGA GGCCCCCGGC CGCCTCAGCC    5500
lAlaAlaLeu ProAlaAlaG lyAlaAlaGl uAlaProAla ArgLeuSerP

CTGCCATCCC GCTGGAGGCC CTGCGGGACA AGGCACTGAG GATGCTGGGG    5550
roAlaIlePr oLeuGluAla LeuArgAspL ysAlaLeuAr gMetLeuGly

GAGGCGGTGC GCGACGGTGG GCAGCACGCT CGGCGACCCCG TCGGGGCCTC    5600
GluAlaValA rgAspGlyGl yGlnHisAla ArgAspProV alGlyAlaSe

CGTGGAGTTC CAGTTTGTGC CTGTGCTCAA GCTCGTGTCC ACCCTGCTGG    5650
rValGluPhe GlnPheValP roValLeuLy sLeuValSer ThrLeuLeuV

TGATGGGCAT CTTTGGCGAT GAGGATGTGA AACAGATCTT GAAGATGATT    5700
alMetGlyIl ePheGlyAsp GluAspValL ysGlnIleLe uLysMetIle
```

FIG. 20".

```
GAGCCTGAGG  TCTTCACTGA  GGAAGAAGAG  GAGGAGGACG  AGGAGGAAGA  5750
GluProGluV  alPheThrGl  uGluGluGlu  GluGluAspG  luGluGluGl

GGGTGAAGAG  GAAGATGAGG  AGGAGAAGGA  GGAGGATGAG  GAGGAAACAG  5800
uGlyGluGlu  GluAspGluG  luGluLysGl  uGluAspGlu  GluGluThrA

CACAGGAAAA  GGAAGATGAG  GAAAAGAGG   AAGAGGAGGC  AGCAGAAGGG  5850
laGlnGluLy  sGluAspGlu  GluLysGluG  luGluGluAl  aAlaGluGly

GAGAAAGAAG  AAGGCTTGGA  GGAAGGGCTG  CTCCAGATGA  AGTTGCCAGA  5900
GluLysGluG  luGlyLeuGl  uGluGlyLeu  LeuGlnMetL  ysLeuProGl

GTCTGTGAAG  TTACAGATGT  GCCACCTGCT  GGAGTATTTC  TGTGACCAAG  5950
uSerValLys  LeuGlnMetC  ysHisLeuLe  uGluTyrPhe  CysAspGlnG

AGCTGCAGCA  CCGTGTGGAG  TCCCTGGCAG  CCTTTGCGGA  GCGCTATGTG  6000
luLeuGlnHi  sArgValGlu  SerLeuAlaA  laPheAlaGl  uArgTyrVal

GACAAGCTCC  AGGCCAACCA  GCGGAGCCGC  TATGGCCTCC  TCATAAAAGC  6050
AspLysLeuG  lnAlaAsnGl  nArgSerArg  TyrGlyLeuL  euIleLysAl

CTTCAGCATG  ACCGCAGCAG  AGACTGCAAG  ACGTACCCGC  GAGTTCCGCT  6100
aPheSerMet  ThrAlaAlaG  luThrAlaAr  gArgThrArg  GluPheArgS
```

FIG. 2P.

```
CCCCACCCCA GGAACAGATC AATATGCTAT TGCAATTCAA AGATGGTACA 6150
erProProGl nGluGlnIle AsnMetLeuL euGlnPheLy sAspGlyThr

GATGAGGAAG ACTGTCCTCT CCCTGAAGAG ATTCGACAGG ATTTGCTTGA 6200
AspGluGluA spCysProLe uProGluGlu IleArgGlnA spLeuLeuAs

CTTTCATCAA GACCTGCTGG CACACTGTGG AATTCAGCTA GATGGAGAGG 6250
pPheHisGln AspLeuLeuA laHisCysGl yIleGlnLeu AspGlyGluG

AGGAGGAACC AGAGGAAGAG ACCACCCTGG GCAGCCGCCT CATGAGCCTG 6300
luGluGluPr oGluGluGlu ThrThrLeuG lySerArgLe uMetSerLeu

TTGGAGAAAG TGCGGCTGGT GAAGAGAAAC CTGAGGAGGA 6350
LeuGluLysV alArgLeuVa lLysLysLys GluGluLysP roGluGluGl

GCGGTCAGCA GAGGAGAGCA AACCCCGGTC CCTGCAGGAG CTGGTGTCCC 6400
uArgSerAla GluGluSerL ysProArgSe rLeuGlnGlu LeuValSerH

ACATGGTGGT GCGGCTGGGC CAAGAGGACT TCGTGCAGAG CCCCGAGCTG 6450
isMetValVa lArgTrpAla GlnGluAspP heValGlnSe rProGluLeu

GTGCGGGCCA TGTTCAGCCT CAGTACGACG GGCTGGGTGA 6500
ValArgAlaM etPheSerLe uLeuHisArg GlnTyrAspG lyLeuGlyGl
```

FIG. 2Q.

```
GCTGCTGCGT GCCCTGCTGCC CATCTCACCG TCCTCCGTGG  6550
uLeuLeuArg AlaLeuProA rIleSerPro SerSerValG

AAGACACCAT GAGCCTGCTC GGGCGTACAC GCCAGATCCG CTCGCTGCTC  6600
luAspThrMe tSerLeuLeu rgAlaTyrTh lyGlnIleAr gSerLeuLeu

ATCGTGCAGA TGGGCCCCCA GAGTGCCTCG GGAGGAGAAAC AGAGCATCGG  6650
IleValGlnM etGlyProGl GluCysLeuG nGluGluAsn lnSerIleGl

GAACATCATG AACAACAAAG TCTTCTACCA ACACCCGAAC CTGATGAGGG  6700
yAsnIleMet AsnAsnLysV alPheTyrGl nHisProAsn LeuMetArgA

CGCTGGGCAT GCACGAGACG GTCATGGAGG TCATGGTCAA CGTCCTCGGG  6750
laLeuGlyMe tHisGluThr ValMetGluV alMetValAs nValLeuGly

GGCGGCGAGT CCAAGGAGAT CCGCTTCCCC AAGATGGTGA CAAGCTGCTG  6800
GlyGlyGluS erLysGluIl eArgPhePro LysMetValT hrSerCysCy

CCGCTTCCTC TGCTATTTCT GCCGAATCAG CCGGCAGAAC CAGCGGCTCCA  6850
sArgPheLeu CysTyrPheC ysArgIleSe rArgGlnAsn GlnArgSerM

TGTTTGACCA CCTGAGCTAC ACAGTGGCAT CTGCTGGGC  6900
etPheAspHi sLeuSerTyr LeuLeuGluA snSerGlyIl eGlyLeuGly
```

FIG.2R

```
ATGCAGGGCT CCACGCCCCT GGACGTGGCT GCTGCCTCCG TCATTGACAA    6950
MetGlnGlyS erThrProLe uAspValAla AlaAlaSerV alIleAspAs

CAATGAGCTG GCCTTGGCAT TGCAGGAGCA GGACCTGGAA AAGGTTGTGT    7000
nAsnGluLeu AlaLeuAlaL euGlnGluGl nAspLeuGlu LysValValS

CCTACCTGGC AGGCTGTGGC CTCCAGAGCT GCCCCATGCT GTGGCCAAAA    7050
erTyrLeuAl aGlyCysGly LeuGlnSerC ysProMetLe uValAlaLys

GGGTACCCAG ACATTGGCTG GAAGCCCTGT GGTGGAGAGC GCTACCTGGA    7100
GlyTyrProA spIleGlyTr pLysProCys GlyGlyGluA rgTyrLeuAs

CTTCCTGCGC TTTGCTGTCT TCGTCAACGG CGAGAGCGTG GAGGAGAACG    7150
pPheLeuArg PheAlaValP heValAsnGl yGluSerVal GluGluAsnA

CCAATGTGGT GGTGCGGGCT CTCATCCGGA AGCCTGAGTG CTTCGGACCC    7200
laAsnValVa lValArgLeu LeuIleArgL ysProGluCy sPheGlyPro

GCCCTGCGGG GTGAGGGTGG CTCAGGGCTG CTGGCTGCCA TCGAAGAGGC    7250
AlaLeuArgG lyGluGlyGl ySerGlyLeu LeuAlaAlaI leGluGluAl

CATCCGCATC TCCGAGGACC CTGCGAGGGA TGGCCCAGGG ATCCGCAGGG    7300
aIleArgIle SerGluAspP roAlaArgAs pGlyProGly IleArgArgA
```

FIG.2S.

```
ACCGGCGGCG CGAGCACTTT GGTGAGGAAC CGCCTGAAGA AAACCGGGTG   7350
spArgAr    gGluHisPhe GlyGluGluP roProGluGl uAsnArgVal

CACCTGGGAC ACGCCATCAT GTCCTTCTAT GCCGCCTTGA TCGACCTGCT   7400
HisLeuGlyH isAlaIleMe tSerPheTyr AlaAlaLeuI leAspLeuLe

CGGACGCTGT GCACCAGAGA TGCATCTAAT CCAAGCCGGC AAGGGTGAGG   7450
uGlyArgCys AlaProGluM etHisLeuIl eGlnAlaGly LysGlyGluA

CCCTGCGGAT CCGCGCCATC CTCCGCTCCC TTGTGCCCTT GGAGGACCTT   7500
laLeuArgIl eArgAlaIle LeuArgSerL euValProLe uGluAspLeu

GTGGGCATCA TCAGCCTCCC ACTGCAGATT CCCACCCTGG GCAAAGATGG   7550
ValGlyIleI leSerLeuPr oLeuGlnIle ProThrLeuG lyLysAspGl

GGCTCTGGTG CAGCCAAAGA TGTCAGCATC CTTCGTGCCG GACCACAAGG   7600
yAlaLeuVal GlnProLysM etSerAlaSe rPheValPro AspHisLysA

CGTCCATGGT GCTCTTCCTG GACCGTGTGT ATGGCATCGA GAACCAGGAC   7650
laSerMetVa lLeuPheLeu AspArgValT yrGlyIleGl uAsnGlnAsp

TTCTTGCTGC ACGTGCTGGA CGTGGGGTTC CTGCCCGACA TGAGGGCAGC   7700
PheLeuLeuH isValLeuAs pValGlyPhe LeuProAspM etArgAlaAl
```

FIG.2T.

```
CGCCTCGCTG GACACGGCCA CTTTCAGCAC CACCGAGATG GCGCTGGCCG 7750
aAlaSerLeu AspThrAlaT hrPheSerTh rThrGluMet AlaLeuAlaV

TGAACCGCTA CCTGTGCCTG GCCGTGCTGC CGCTCATCAC CAAGTGTGCG 7800
alAsnArgTy rLeuCysLeu AlaValLeuP roLeuIleTh rLysCysAla

CCGCTCTTTG CGGGCACAGA ACACCCGCCC ATCATGGTGG ACTCTATGCT 7850
ProLeuPheA laGlyThrGl uHisArgAla IleMetValA spSerMetLe

GCATACCGTG TACCGCCTGT CTCGGGGTCG TTCGCTCACC AAGGCGCAGC 7900
uHisThrVal TyrArgLeuS erArgGlyAr gSerLeuThr LysAlaGlnA

GTGACGTCAT CGAGGACTGC CTCATGTCGC TCTGCAGGTA CATCCGCCCG 7950
rgAspValIl eGluAspCys LeuMetSerL euCysArgTy rIleArgPro

TCGATGCTGC AGCACCTGTT GCGCCGCCTG GTGTTCGACG TGCCCATCCT 8000
SerMetLeuG lnHisLeuLe uArgArgLeu ValPheAspV alProIleLe

CAACGAGTTC GCCAAGATGC CACTCAAGCT CCTCACCAAC CACTATGAGC 8050
uAsnGluPhe AlaLysMetP roLeuLysLe uLeuThrAsn HisTyrGluA

GCTGTTGGAA GTACTACTGC CTACCCACGG GCTGGGCCAA CTTCGGGGTC 8100
rgCysTrpLy sTyrTyrCys LeuProThrG lyTrpAlaAs nPheGlyVal
```

FIG.2U.

```
ACCTCAGAGG AGGAGCTGCA CCTCACACGG AAACTCTTCT GGGGCATCTT 8150
ThrSerGluG luGluLeuHi sLeuThrArg LysLeuPheT rpGlyIlePh

TGACTCTCTG GCCCATAAGA AATACGACCC GGAGCTGTAC CGCATGGCCA 8200
eAspSerLeu AlaHisLysL ysTyrAspPr oGluLeuTyr ArgMetAlaM

TGCCTTGTCT GTGCGCCATT GCCGGGGCTC TGCCCCCCGA CTATGTGGAT 8250
etProCysLe uCysAlaIle AlaGlyAlaL euProProAs pTyrValAsp

GCCTCATACT CATCTAAGGC AGAGAAAAAG GCCACAGTGG ATGCTGAAGG 8300
AlaSerTyrS erSerLysAl aGluLysLys AlaThrValA spAlaGluGl

CAACTTTGAT CCCCGGCCTG TGGAGACCCT CAATGTGATC ATCCCGGAGA 8350
yAsnPheAsp ProArgProV alGluThrLe uAsnValIle IleProGluL

AGCTGGACTC CTTCATTAAC AAGTTTGCGG AGTACACACA CGAGAAGTGG 8400
ysLeuAspSe rPheIleAsn LysPheAlaG luTyrThrHi sGluLysTrp

GCCTTCGACA AGATCCAGAA CAACTGGTCC TATGGAGAGA ACATAGACGA 8450
AlaPheAspL ysIleGlnAs nAsnTrpSer TyrGlyGluA snIleAspGl

GGAGCTGAAG ACCCACCCCA TGCTGAGGCC CTACAAGACC TTTTCAGAGA 8500
uGluLeuLys ThrHisProM etLeuArgPr oTyrLysThr PheSerGluL
```

FIG.2V.

```
AGGACAAAGA GATTTACCGC TGGCCCATCA AGGAGTCCCT GAAGGCCATG 8550
ysAspLysGl uIleTyrArg TrpProIleL ysGluSerLe uLysAlaMet

ATTGCCTGGG AATGGACGAT AGAGAAGGCC AGGGAGGGTG AGGAGGAGAA 8600
IleAlaTrpG luTrpThrIl eGluLysAla ArgGluGlyG luGluGluLy

GACGGAAAAG AAAAAAACGG CGAAGATATC ACAAAGTGCC CAGACCTATG 8650
sThrGluLys LysLysThrA laLysIleSe rGlnSerAla GlnThrTyrA

ATCCTCGAGA AGGCTACAAC CCTCAGCCCC CCGACCTTAG TGCTGTTACC 8700
spProArgGl uGlyTyrAsn ProGlnProP roAspLeuSe rAlaValThr

CTGTCCCGGG AGCTGCAGGC CATGGCAGAA CAACTGGCAG AAAATTACCA 8750
LeuSerArgG luLeuGlnAl aMetAlaGlu GlnLeuAlaG luAsnTyrHi

CAACACGTGG GGACGGAAGA AGAAGCAGGA GCTGGAAGCC AAAGGCGGTG 8800
sAsnThrTrp GlyArgLysL ysLysGlnGl uLeuGluAla LysGlyGlyG

GGACCCACCC CCTGCTGGTC CCCTACGACA CGCTCACGGC CAAGGAGAAG 8850
lyThrHisPr oLeuLeuVal ProTyrAspT hrLeuThrAl aLysGluLys

GCACGAGATC GAGAGAAGGC CCAGGAGGTA CTGAAATTCC TGCAGATGAA 8900
AlaArgAspA rgGluLysAl aGlnGluLeu LeuLysPheL euGlnMetAs
```

FIG. 2W.

```
TGGCTACGCG GTTACAAGAG GCCTTAAGGA CATGGAACTG GACTCGTCTT 8950
nGlyTyrAla ValThrArgG lyLeuLysAs pMetGluLeu AspSerSerS

CCATTGAAAA GCGGTTTGCC TTTGGCTTCC TGCAGCAGCT GCTGCGCTGG 9000
erIleGluLy sArgPheAla PheGlyPheL euGlnGlnLe uLeuArgTrp

ATGGACATTT CTCAGGAGTT CATTGCCCAC CTGGAGGCTG TGGTCAGCAG 9050
MetAspIleS erGlnGluPh eIleAlaHis LeuGluAlaV alValSerSe

TGGGCGAGTG GAAAAGTCCC CACATGAACA GGAGATTAAA TCACCAACCA 9100
rGlyArgVal GluLysSerP roHisGluGl nGluIleLys heThrAsnHi

AGATCCTGCT CCCTTTGATC AACCAGTACT AGCGGTGGCC CTGCCTCTAT 9150
sIleLeuLeu uProLeuIle AsnGlnTyrP SerGlyGlyH isCysLeuTyr

TTCTTGTCCA CTCCGGCTAA AGTGCTGGGC CCAGCCTCTT ACGCCTCTAA 9200
PheLeuSerT hrProAlaLy sValLeuGly ProAlaSerL ysAlaSerAs

CAAGGAGAAG GAAATGATCA GAAATGATCA CCAGCCTCTT CTGCAAACTT GCTGCTCTCG 9250
nLysGluLys GluMetIleT hrSerLeuPh eCysLysLeu AlaAlaLeuV

TCCGCCACCG AGTCTCTCTC TTTGGGACAG ACGCCCCAGC TGTGGTCAAC 9300
alArgHisAr gValSerLeu PheGlyThrA spAlaProAl aValValAsn
```

FIG.2X.

```
TGTCTTCACA TCCTGGCCCG CTCCCTGGAT GCCAGGACAG TGATGAAGTC 9350
CysLeuHisI leLeuAlaAr gSerLeuAsp AlaArgThrV alMetLysSe

AGGCCCTGAG ATCGTGAAGG CTGGCCTCCG CTCCTTCTTC GAGAGTGCCT 9400
rGlyProGlu IleValLysA laGlyLeuAr gSerPhePhe GluSerAlaS

CGAGGACAT CGAGAAGATG GTGGAGAACC TGCGGCTGGG CAAGGTGTCG 9450
erGluAspIl eGluLysMet ValGluAsnL euArgLeuGl yLysValSer

CAGGGCCGCA CCCAGGTGAA AGGCGTGGGC CAGAACCTCA CCTACACCAC 9500
GlnAlaArgT hrGlnValLy sGlyValGly GlnAsnLeuT hrTyrThrTh

TGTGGCACTG CTGCCGGTCC TCACCACCCT CTTCCAGCAC ATCGCCCAGC 9550
rValAlaLeu LeuProValL euThrThrLe uPheGlnHis IleAlaGlnH

ACCAGTTCGG AGATGACGTC ATCCTGGACG ACGTCCAGGT CTCTTGCTAC 9600
isGlnPheGl yAspAspVal IleLeuAspA spValGlnVa lSerCysTyr

CGAACGCTGT GCAGTATCTA CTCCCTGGGA ACCACCAAGA ACACTTATGT 9650
ArgThrLeuC ysSerIleTy rSerLeuGly ThrThrLysA snThrTyrVa

GGAAAAGCTT CGGCCAGCCC TCGGGGAGTG CCTGGCCCGT CTGGCAGCAG 9700
lGluLysLeu ArgProAlaL euGlyGluCy sLeuAlaArg LeuAlaAlaA
```

FIG. 2Y.

```
CCATGCCGGT GGCGTTCCTG GAGCCGCAGC TGAACGAGTA CAACGCCTGC      9750
laMetProVa lAlaPheLeu GluProGlnL euAsnGluTy rAsnAlaCys

TCCGTGTACA CCACCAAGTC TCCGCGGGAG CGGGCCATCC TGGGGCTCCC      9800
SerValTyrT hrThrLysSe rProArgGlu ArgAlaIleL euGlyLeuPr

CAACAGTGTG GAGGAGATGT GTCCCGACAT CCCGGTGCTG GAGCGGGCTCA     9850
oAsnSerVal GluGluMetC ysProAspIl eProValLeu GluArgLeuM

TGGCAGACAT GCCGAGTCAG GTGCCCGCTA CACAGAGATG                 9900
etAlaAspIl eGlyGlyLeu AlaGluSerG lyAlaArgTy rThrGluMet

CCGCATGTCA TCGAGATCAC GCTGCCCATG CTATGCAGCT ACCTGCCCCG      9950
ProHisValI leGluIleTh rLeuProMet LeuCysSerT yrLeuProAr

ATGGTGGGAG CGCGGGCCCG AGGCACCCCG TTCCGCCCTG CCCGCCGGGCG    10000
gTrpTrpGlu ArgGlyProG luAlaProPr oSerAlaLeu ProAlaGlyA

CCCCCCCACC CTGCACAGCT GTCACCTCTG ACCACCTCAA CTCCCTGCTG     10050
laProProPr oCysThrAla ValThrSerA spHisLeuAs nSerLeuLeu

GGGAATATCC TGAGAATCAT CGTCAACAAC CTGGGCATTG ACGAGGCCTC     10100
GlyAsnIleL euArgIleIl eValAsnAsn LeuGlyIleA spGluAlaSe
```

FIG. 2Z.

```
CTGGATGAAG CGGCTGGCTG TGTTCGCACA GCCCATTGTG AGCCGTGCAC 10150
rTrpMetLys ArgLeuAlaV alPheAlaGl nProIleVal SerArgAlaA

GGCCGGAGCT CCTGCAGTCC CACTTCATCC CAACTATCGG GCGGCTGCGC 10200
rgProGluLe uLeuGlnSer HisPheIleP roThrIleGl yArgLeuArg

AAGAGGGCAG GGAAGGTGGT GTCCGAGGAG GAGCAGCTGG CCCTGGAGGC 10250
LysArgAlaG lyLysValVa lSerGluGlu GluGlnLeuA laLeuGluAl

CAAGGCGGAG GCCCAGGAGG GCGAGCTGCT GGTGCGGGAC GAGTTCTCTG 10300
aLysAlaGlu AlaGlnGluG lyGluLeuLe uValArgAsp GluPheSerV

TGCTCTGCCG GGACCTCTAC GCCCTGTATC CGCTGCTCAT CCGCTACGTG 10350
alLeuCysAr gAspLeuTyr AlaLeuTyrP roLeuLeuIl eArgTyrVal

GACAACAACA GGGCGCAGTG GCTGACGGAG CCGAATCCCA GCGCGGAGGA 10400
AspAsnAsnA rgAlaGlnTr pLeuThrGlu ProAsnProS erAlaGluGl

GCTGTTCAGG ATGGTGGGCG AGATCTTCAT CTACTGGTCC AAGTCCCACA 10450
uLeuPheArg MetValGlyG luIlePheIl eTyrTrpSer LysSerHisA

ACTTCAAGCG CGAGGAGCAG AACTTTGTGG TCCAGAATGA GATCAACAAC 10500
snPheLysAr gGluGluGln AsnPheValV alGlnAsnGl uIleAsnAsn
```

FIG. 2A-1

```
ATGTCCTTCC TGACTGCTGA CAACAAAAGC AAAATGGCTA AGTCCGGTGG 10550
MetSerPheL euThrAlaAs pAsnLysSer LysMetAlaL ysSerGlyGl

CTCGGACCAG GAACGCACCA AGAAGAAGCG CCGGGGGGAC CGGTACTCTG 10600
ySerAspGln GluArgThrL ysLysLysAr gArgGlyAsp ArgTyrSerV

TGCAGACGTC ACTGATCGTG GCCACACTGA AGAAGATGCT GCCCATCGGC 10650
alGlnThrSe rLeuIleVal AlaThrLeuL ysLysMetLe uProIleGly

CTGAATATGT GTGCGCCCAC CGACCAAGAC CTCATCACGC TGGCCAAGAC 10700
LeuAsnMetC ysAlaProTh rAspGlnAsp LeuIleThrL euAlaLysTh

CCGTTACGCC CTGAAAGACA CAGATGAGGA GGTCCGGGAA TTTCTGCACA 10750
rArgTyrAla LeuLysAspT hrAspGluGl uValArgGlu PheLeuHisA

ACAACCTTCA CCTTCAGGGA AAGGTCGAAG GCTCCCCGTC TCTGCGCTGG 10800
snAsnLeuHi sLeuGlnGly LysValGluG lySerProSe rLeuArgTrp

CAGATGGCTC TGTACCGGGG CGTCCCGGGT CGCGAGGAGG ACGCCGATGA 10850
GlnMetAlaL euTyrArgGl yValProGly ArgGluGluA spAlaAspAs

CCCGAGAAA ATCGTGCGCA GAGTCCAGGA AGTGTCAGCC GTGCTCTACT 10900
pProGluLys IleValArgA rgValGlnGl uValSerAla ValLeuTyrT
```

FIG. 2A-2

```
ACCTGGACCA GACCGAGCAC CCTTACAAGT CTAAGAAGGC CGTGTGGCAC 10950
yrLeuAspGl nThrGluHis ProTyrLysS erLysLysAl aValTrpHis

AAGCTTTTGT CCAAACAGCG CCGGCGGGCA GTCGTGGCCT GTTTCCGTAT 11000
LysLeuLeuS erLysGlnAr gArgArgAla ValValAlaC ysPheArgMe

GACGCCCCTG TACAACCTGC CCACGCACCG GGCATGTAAC ATGTTCCTGG 11050
tThrProLeu TyrAsnLeuP roThrHisAr gAlaCysAsn MetPheLeuG

AGAGCTACAA GGCTGCATGG ATCCTGACTG AAGACCACAG TTTTGAGGAC 11100
luSerTyrLy sAlaAlaTrp IleLeuThrG luAspHisSe rPheGluAsp

CGGATGATAG ATGACCTTTC AAAAGCTGGG GAGCAGGAGG AGGAGGAGGA 11150
ArgMetIleA spAspLeuSe rLysAlaGly GluGlnGluG luGluGluGl

AGAGGTGGAA GAGAAGAAGC CAGACCCCCT GCACCAGTTG GTCCTGCACT 11200
uGluValGlu GluLysLysP roAspProLe uHisGlnLeu ValLeuHisP

TCAGCCGCAC TGCCCTGACG GAAAAGAGCA AACTGGATGA GGATTACCTG 11250
heSerArgTh rAlaLeuThr GluLysSerL ysLeuAspGl uAspTyrLeu

TACATGGCCT ATGCTGATAT CATGGCAAAG AGCTGCCACC TGGAGGAGGG 11300
TyrMetAlaT yrAlaAspIl eMetAlaLys SerCysHisL euGluGluGl
```

FIG.2A-3

```
AGGGGAGAAC  GGTGAAGCTG  AAGAGGAGGT  TGAGGTCTCC  TTTGAGGAGA  11350
yGlyGluAsn  GlyGluAlaG  luGluGluVa  lGluValSer  PheGluGluL

AACAGATGGA  GAAGCAGAGG  CTCTTGTACC  AGCAAGCACG  GCTGCACACC  11400
ysGlnMetGl  uLysGlnArg  LeuLeuTyrG  lnGlnAlaAr  gLeuHisThr

CGGGGGGCGG  CCGAGATGGT  GCTGCAGATG  ATCAGTGCCT  GCAAAGGAGA  11450
ArgGlyAlaA  laGluMetVa  lLeuGlnMet  IleSerAlaC  ysLysGlyGl

GACAGGTGCC  ATGGTGTCCT  CCACCCTGAA  GCTGGGCATC  TCCATCCTCA  11500
uThrGlyAla  MetValSerS  erThrLeuLy  sLeuGlyIle  SerIleLeuA

ATGGAGGCAA  TGCTGAGGTC  CAGCAGAAAA  TGCTGGATTA  TCTTAAGGAC  11550
snGlyGlyAs  nAlaGluVal  GlnGlnLysM  etLeuAspTy  rLeuLysAsp

AAGAAGGAAG  TTGGCTTCTT  CCAGAGTATC  CAGGCACTGA  TGCAAACATG  11600
LysLysGluV  alGlyPhePh  eGlnSerIle  GlnAlaLeuM  etGlnThrCy

CAGCGTCCTG  GATCTCAATG  CCTTTGAGAG  ACAGAACAAG  GCCGAGGGGC  11650
sSerValLeu  AspLeuAsnA  laPheGluAr  gGlnAsnLys  AlaGluGlyL

TGGGCATGGT  GAATGAGGAT  GGCACTGTCA  TCAATCGCCA  GAACGGAGAG  11700
euGlyMetVa  lAsnGluAsp  GlyThrVall  leAsnArgGl  nAsnGlyGlu
```

FIG.2A-4

```
AAGGTCATGG CGGATGATGA ATTCACACAA GACCTGTTCC GATTCCTACA 11750
LysValMetA laAspAspGl uPheThrGln AspLeuPheA rgPheLeuGl

ATTGCTCTGT GAGGGGCACA ATAATGATTT CCAGAACTAC CTACGGACAC 11800
nLeuLeuCys GluGlyHisA snAsnAspPh eGlnAsnTyr LeuArgThrG

AGACAGGGAA CACGACCACT ATTAACATCA TCATTTGCAC TGTGGACTAC 11850
lnThrGlyAs nThrThrThr IleAsnIleI leIleCysTh rValAspTyr

CTCCTGCGGC TGCAGGAATC CATCAGCGAC TTCTACTGGT ACTACTCGGG 11900
LeuLeuArgL euGlnGluSe rIleSerAsp PheTyrTrpT yrTyrSerGl

CAAGGATGTC ATTGAAGAGC AGGGCAAGAG GAACTTCTCC AAAGCCATGT 11950
yLysAspVal IleGluGluG lnGlyLysAr gAsnPheSer LysAlaMetS

CGGTGGCTAA GCAGGTGTTC AACAGCCTCA CTGAGTACAT CCAGGGTCCC 12000
erValAlaLy sGlnValPhe AsnSerLeuT hrGluTyrIl eGlnGlyPro

TGCACCGGGA ACCAGCAGAG CCTGGGCCAC AGTCGCCTAT GGGACGCAGT 12050
CysThrGlyA snGlnGlnSe rLeuAlaHis SerArgLeuT rpAspAlaVa

GGTGGGATTC CTGCACGTGT TCGCCCACAT GATGATGAAG CTCGCTCAGG 12100
lValGlyPhe LeuHisValP heAlaHisMe tMetMetLys LeuAlaGlnA
```

FIG.2A5

```
ACTCAAGCCA GATCGAGCTG CTGAAGGAGC TGCTGGATCT GCAGAAGGAC  12150
spSerSerGl nIleGluLeu LeuLysGluL euLeuAspLe uGlnLysAsp

ATGGTGGTGA TGTTGCTGTC GCTACTAGAA GGGAACGTGG TGAACGGCAT  12200
MetValValM etLeuLeuSe rLeuLeuGlu GlyAsnValV alAsnGlyMe

GATCGCCCGG CAGATGGTGG ACATGCTCGT GGAATCCTCA TCCAATGTGG  12250
tIleAlaArg GlnMetValA spMetLeuVa lGluSerSer SerAsnValG

AGATGATCCT CAAGTTCTTC GACATGTTCC TGAAACTCAA GGACATTGTG  12300
luMetIleLe uLysPhePhe AspMetPheL euLysLeuLy sAspIleVal

GGCTCTGAAG CCTTCCAGGA CTACGTAACG GATCCCCGTG GCCTCATCTC  12350
GlySerGluA laPheGlnAs pTyrValThr AspProArgG lyLeuIleSe

CAAGAAGGAC TTCCAGAAGG CCATGGACAG CCAGAAGCAG TTCAGCGGTC  12400
rLysLysAsp PheGlnLysA laMetAspSe rGlnLysGln PheSerGlyP

CAGAAATCCA GTTCCTGCTT TCGTGCTCCG AAGCGGATGA GAACGAAATG  12450
roGluIleGl nPheLeuLeu SerCysSerG luAlaAspGl uAsnGluMet

ATCAACTGCG AAGAGTTCGC CAACCGCTTC CAGGAGCCAG CACGCGACAT  12500
IleAsnCysG luGluPheAl aAsnArgPhe GlnGluProA laArgAspIl
```

FIG.2A-6

```
CGGCTTCAAC GTGGCGGTGC TGCTGACCAA CCTGTCGGAG CATGTGCCGC  12550
eGlyPheAsn ValAlaValL euLeuThrAs nLeuSerGlu HisValProH

ATGACCCTCG CCTGCACAAC TTCCTGGAGC TGGCCGAGAG CATCCTTGAG  12600
isAspProAr gLeuHisAsn PheLeuGluL euAlaGluSe rIleLeuGlu

TACTTCCGCC CCTACCTGGG ATCATGGGCG CCGCATCGAG CGTCACGCCG  12650
TyrPheArgP roTyrLeuGl yArgIleGlu IleMetGlyA laSerArgAr

CATCGAGCGC ATCTACTTCG AGATCTCAGA GACCAACCGC GCCCAGTGGG  12700
gIleGluArg IleTyrPheG luIleSerGl uThrAsnArg AlaGlnTrpG

AGATGCCCCA GGTGAAGGAG TCCAAGCGCC AGTTCATCTT CGACGTGGTG  12750
luMetProGl nValLysGlu SerLysArgG lnPheIlePh eAspValVal

AACGAGGGCG GCGAGGCTGA GAAGATGGAG CTCTTCGTGA GTTTCTGCGA  12800
AsnGluGlyG lyGluAlaGl uLysMetGlu LeuPheValS erPheCysGl

GGACACCATC TTCGAGATGC AGATCGCCGC AGATCTCGCC GAGCCCGAGG  12850
uAspThrIle PheGluMetG lnIleAlaAl aGlnIleSer GluProGluG

GCGAGCCGGA GACCGACGAG CGGGGCGGGC GGGGCGGCGG GGAGGCGGGC  12900
lyGluProGl uThrAspGlu AspGluGlyA laGlyAlaAl aGluAlaGly
```

FIG. 2A-7

```
GCGGAAGGCG CGGAGGAGGG CGCGGGCGGG CTCGAGGGCA CGGGGGCCAC 12950
AlaGluGlyA laGluGluGl yAlaAlaGly LeuGluGlyT hrAlaAlaTh

GGCGGCGGCG GGGGCGACGG GGCGGGTTGT CGCGGCCGCA GGCCGGGCCC 13000
rAlaAlaAla GlyAlaThrA laArgValVa lAlaAlaAla GlyArgAlaL

TGCGGAGGCT CAGCTACCGC AGCCTGCGCC GGCGCGTGCG GCCGCTGCGG 13050
euArgGlyLe uSerTyrArg SerLeuArgA rgArgValAr gArgLeuArg

CGGCTTACGG CCCGCGAGGC GGCCACCGCA GTGGCGGCGC TGCTCTGGGC 13100
ArgLeuThrA laArgGluAl aAlaThrAla ValAlaAlaL euLeuTrpAl

AGCAGTGACG CGGCTGGGGG CCGCTGGCGC GGGGCGGGCG GCGGGCCGCG 13150
aAlaValThr ArgAlaGlyA laAlaGlyAl aGlyAlaAla AlaGlyAlaL

TGGGCCTGCT CTGGGGCTCG CTGTTCGGCG GCGGCCTGGT GGAGGGCGCC 13200
euGlyLeuLe uTrpGlySer LeuPheGlyG lyGlyLeuVa lGluGlyAla

AAGAAGGTGA CGGTGACCGA GCTCCTGGCA GGCATGCCCG ACCCCACCAG 13250
LysLysValT hrValThrGl uLeuLeuAla GlyMetProA spProThrSe

CGACGAGGTG CACGGCGAGC AGCCGGGCCG GCCGGGCGGA GACGCAGACG 13300
rAspGluVal HisGlyGluG lnProAlaGl yProGlyGly AspAlaAspG
```

FIG.2A-8

```
GCGAGGGTGC CAGCGGAGGGC GCTGGAGACG CCGCGGGAGG CGCTGGAGAC 13350
 lyGluGlyAl aSerGluGly AlaGlyAspA laAlaGluGl yAlaGlyAsp

GAGGAGGAGG CGGTGCACGA GGCCCGGGCCA GGCCGGTGCCG ACGGGGCGGT 13400
 GluGluGluA laValHisGl uAlaGlyPro GlyGlyAlaA spGlyAlaVa

GGCCGTGACC GATGGGGGCC CCTTCCGGCC CGAAGGGGCT GGCGGTCTCG 13450
 lAlaValThr AspGlyGlyP roPheArgPr oGluGlyAla GlyGlyLeuG

GGACACATGG GGACACGACG CCTGCGGAAC CGCCCACACC CGAGGGCTCT 13500
 lyAspMetGl yAspThrThr ProAlaGluP roProThrPr oGluGlySer

CCCATCCTCA AGAGGAAATT GGGGGTGGAT GGAGTGGAGG AGGAGCTCCC 13550
 ProIleLeuL ysArgLysLe uGlyValAsp GlyValGluG luGluLeuPr

GCCAGAGCCA GAGCCCGAGC CGGAACCAGA GCTGGAGCCG GAGAAAGCCG 13600
 oProGluPro GluProGluP roGluProGl uLeuGluPro GluLysAlaA

ATGCCGAGAA TGGGGAGAAG GAAGAAGTTC GAGGAGGTC ACCAGAGCCCAC 13650
 spAlaGluAs nGlyGluLys GluGluValP roGluProTh rProGluPro

CCCAAGAAGC AAGCACCTTC CTCACCCCCT CCAAAGAAGG AGGAAGCTGG 13700
 ProLysLysG lnAlaProPr oSerProPro ProLysLysG luGluAlaGl
```

FIG.2A-9

```
AGGCGAATTC TGGGAGAAAC TGGAGGTGCA GAGGGTGAAG TTCCTGAACT 13750
yGlyGluPhe TrpGlyGluL euGluValGl nArgValLys PheLeuAsnT

ACCTGTCCCG GAACTTTTAC ACCCTGCGGT TCCTTGCCCT CTTCTTGGCA 13800
yrLeuSerAr gAsnPheTyr ThrLeuArgP heLeuAlaLe uPheLeuAla

TTTGCCATCA ACTTCATCTT GCTGTTTTAT AAGGTCTCAG ACTCTCCACC 13850
PheAlaIleA snPheIleLe uLeuPheTyr LysValSerA spSerProPr

AGGGGAGGAC GACATGGAAG GCTCAGCTGC TGGGGATGTG TCAGGTGCAG 13900
oGlyGluAsp AspMetGluG lySerAlaAl aGlyAspVal SerGlyAlaG

GCTCTGGTGG CAGCTCTGGC TGGGGCTTGG GGGCCGGAGA GGAGGCAGAG 13950
lySerGlyGl ySerSerGly TrpGlyLeuG lyAlaGlyGl uGluAlaGlu

GGCGATGAGG ATGAGAACAT GGTGTACTAC TTCCTGGAGG AAAGCACAGG 14000
GlyAspGluA spGluAsnMe tValTyrTyr PheLeuGluG luSerThrGl

CTACATGGAA CCCGCCCCTG CCTGTCTGAG CCTCCCTGCAT ACACTGGTGG 14050
yTyrMetGlu ProAlaLeuA rgCysLeuSe rLeuLeuHis ThrLeuValA

CCTTTCTCTG CATCATTGGC TATAATTGTC TCAAGGTGCC CCTGGTAATC 14100
laPheLeuCy sIleIleGly TyrAsnCysL euLysValPr oLeuValIle
```

FIG. 2A-10

```
TTTAAGCGGG AGAAGGAGCT GGCCCGGAAG CTGGAGTTTG ATGGCCTGTA 14150
PheLysArgG luLysGluLe uAlaArgLys LeuGluPheA spGlyLeuTy

CATCACGGAG CAGCCTGAGG ACGATGACGT GAAGGGGCAG TGGGACCGAC 14200
rIleThrGlu GlnProGluA spAspAspVa lLysGlyGln TrpAspArgL

TGGTGCTCAA CACGCCGTCT TTCCCTAGCA ACTACTGGGA CAAGTTTGTC 14250
euValLeuAs nThrProSer PheProSerA snTyrTrpAs pLysPheVal

AAGCGCAAGG TCCTGGACAA ACATGGGGAC ATCTACGGGC GGGAGCGGAT 14300
LysArgLysV alLeuAspLy sHisGlyAsp IleTyrGlyA rgGluArgIl

TGCTGAGCTA CTGGGCATGG ACCTGGCCAC ACTAGAGATC ACAGCCCACA 14350
eAlaGluLeu LeuGlyMetA spLeuAlaTh rLeuGluIle ThrAlaHisA

ATGAGCGCAA GCCCAACCCG CCGCCAGGGC TGCTGACCTG GCTCATGTCC 14400
snGluArgLy sProAsnPro ProProGlyL euLeuThrTr pLeuMetSer

ATCGATGTCA AGTACCAGAT CTGGAAGTTC GGGGTCATCT TCACAGACAA 14450
IleAspValL ysTyrGlnIl eTrpLysPhe GlyValIleP heThrAspAs

CTCCTTCCTG TACCTGGGCT GGTATATGGT GATGTCCCTC TTGGGACACT 14500
nSerPheLeu TyrLeuGlyT rpTyrMetVa lMetSerLeu LeuGlyHisT
```

FIG.2A-11

```
ACAACAACTT CTTCTTTGCT GCCCATCTCC TGGACATGCG CATGGGGGTC 14550
yrAsnAsnPh ePheFheAla AlaHisLeuL euAspIleAl aMetGlyVal

AAGACGCTGC GCACCATCCT GTCCTCTGTC ACCCACAATG GGAAACAGCT 14600
LysThrLeuA rgThrIleLe uSerSerVal ThrHisAsnG lyLysGlnLe

GGTGATGACC GTGGGCCTTC TGGCGGTGGT CGTCTACCTG TACACCGTGG 14650
uValMetThr ValGlyLeuL euAlaValVa lValTyrLeu TyrThrValV

TGGCCTTCAA CTTCTTCCGC AAGTTCTACA ACAAGAGCGA GGATGAGGAT 14700
alAlaPheAs nPhePheArg LysPheTyrA snLysSerGl uAspGluAsp

GAACCTGACA TGAAGTGTGA TGACATGATG ACGTGTTACC TGTTTCACAT 14750
GluProAspM etLysCysAs pAspMetMet ThrCysTyrL euPheHisMe

GTACGTGGGT GTCCGGGCTG GCGGAGGCAT TGGGGACGAG ATCGAGGACC 14800
tTyrValGly ValArgAlaG lyGlyGlyIl eGlyAspGlu IleGluAspP

CCGCGGGTGA CGAATACGAG CTCTACAGGG TGGTCTTCGA CATCACCTTC 14850
roAlaGlyAs pGluTyrGlu LeuTyrArgV alValPheAs pIleThrPhe

TTCTTCTTCG TCATCGTCAT CCTGTTGGCC ATCATCCAGG GTCTGATCAT 14900
PhePhePheV alIleValIl eLeuLeuAla IleIleGlnG lyLeuIleIl
```

FIG.2A-12
```
CGACGCTTTT GGTGAGCTCC GAGACCAACA AGAGCAAGTG AAGGAGGATA   14950
eAspAlaPhe GlyGluLeuA rgAspGlnGl nGluGlnVal LysGluAspM

TGGAGACCAA GTGCTTCATC TGTGGAATCG GCAGTGACTA CTTTGATACG   15000
etGluThrLy sCysPheIle CysGlyIleG lySerAspTy rPheAspThr

ACACCGCATG GCTTCGAGAC TCACACGCTG GAGGAGCACA ACCTGGCCAA   15050
ThrProHisG lyPheGluTh rHisThrLeu GluGluHisA snLeuAlaAs

TTACATGTTT TTCCTGATGT ATTTGATAAA CAAGGATGAG ACAGAACACA   15100
nTyrMetPhe PheLeuMetT yrLeuIleAs nLysAspGlu ThrGluHisT

CGGGTCAGGA GTCTTATGTC TGGAAGATGT ACCAAGAGAG ATGTTGGGAT   15150
hrGlyGlnGl uSerTyrVal TrpLysMetT yrGlnGluAr gCysTrpAsp

TTCTTCCCAG CTGGTGATTG TTTCCGTAAG CAGTATGAGG ACCAGCTTAG   15200
PhePheProA laGlyAspCy sPheArgLys GlnTyrGluA spGlnLeuSe

CTGACACACC CCCAGCTGGC CCTCCACCCC CACCTCAAGT GCCTTATTCT   15250
r...

CACAGCAAGC CCCTTAGTCC CCCCCTAAGG CCAAGCCCCT CAGCTGGGGG   15300

AGAGGTGACC TAGTACTGGA AAATAAATCT GTCGTACGCC CCCCA
```

FIG.5A.
MH FAMILY 5
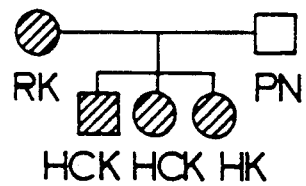
FIG.5B.
MH FAMILY 12
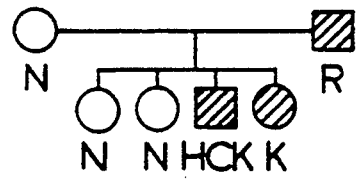
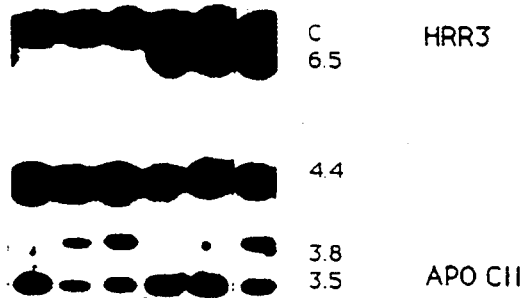

DIAGNOSIS FOR MALIGNANT HYPERTHERMIA

FIELD OF THE INVENTION

This invention relates to the animal disease malignant hyperthermia (MH) and to the cloning and characterization of a gene associated with (MH), and to the development of methods for detecting individuals susceptible to MH.

BACKGROUND OF THE INVENTION

Although malignant hyperthermia is associated primarily with humans and was first realized as a reaction to inhalation anaesthetics, it is understood that MH is also a very common problem in certain animals, particularly pigs. There is therefore particular commercial interest in developing suitable assays to determine MH in pigs, as well as providing suitable diagnosis to test humans to avoid life threatening circumstances in the operating room.

Malignant hyperthermia (MH) is an inherited predisposition to a hypermetabolic syndrome (adverse reaction) triggered by inhalation anaesthetics such as halothane and some skeletal muscle relaxants such as succinylcholine. The primary defect in MH is related to a sustained increase in myoplasmic calcium which causes muscle contracture and increased glycolysis concomitant with the production of $H_2O$, $CO_2$ and heat and excessive consumption of $O_2$. Other signs of the disorder (including the hyperthermia for which it was named) may be explained as a direct result of muscle contracture and increased glycolysis [Steward, D. J. and O'Connor, G. A. R, "Malignant Hyperthermia—The Acute Crisis", in Britt B. A. ed. *Malignant Hyperthermia*, Boston, Martinus Nijhoff, (1987)].

The disease in humans is a serious health problem as the affected individuals are usually unaware of their condition and problem with a potentially lethal reaction to the drugs administered at surgery. The observed frequency of the disease is dependent on the drugs administered. The highest estimate based on the use of succinylcholine in combination with halothane, gives a frequency of 1 in 4200 anaesthetics [Ording, H., *Anesth Analg.* 64: 700–704, (1985)]. This may be a gross underestimate of the true gene frequency since many individuals who carry the gene are never exposed to the triggering agent and thus remain undiagnosed. Additionally the incidence of masseter muscle spasm following halothane-succinylcholine induction of anaesthesia is 1 in 200; 50% of these individuals have been subsequently shown to have biopsies positive for MH suggesting that the true incidence of the trait may be considerably higher [Rosenberg, H, and Fletcher, J. E., *Anesth. Analg.* 65: 161–164, (1986)]. In many families the disease segregates as an autosomal dominant condition [Kalow, W., "Inheritance of Malignant Hyperthermia—A review of Published Data", in Britt, B. A. Ed. *Malignant Hyperthermia*, supra, (1987)] although other modes of inheritance have been reported in some families.

The mortality rate for MH in North America has decreased from 84% in the 1960s to about 7% [Britt, B. A., "Preface: A History of Malignant Hyperthermia", in Britt B. A. ed. *Malignant Hyperthermia*, Boston, Martinus Nijhoff, pp 1–10, (1987)], following improvements in monitoring systems, increased awareness of MH and the advent of dantrolene treatment in 1975. A marked elevation in end-tidal (exhaled) carbon dioxide levels is an early indicator of an MH reaction and, where monitored and recognized, may allow prompt treatment with sodium dantrolene (dantrium) to avert a full crisis. The fatality rate is still unacceptably high in many countries in the world ( e.g. 24% in the U.K.).

Fatalities may result from one or more of multiple complications in a fulminant MH crisis. Skeletal muscle, smooth (involuntary) muscle and cardiac muscle are all affected in an MH reaction. Contraction of smooth muscle of the blood vessels causes hypertension which further decreases the oxygen supply and results in accelerated deep breathing. Pulmonary edema may occur as the crisis progresses especially at the onset of cardiac failure. Cardiac failure is triggered both by rigidity of the heart muscle and by elevated levels of potassium in the blood. Once the temperature of an affected individual has begun to rise it does so rapidly (1° C. every five minutes) and final temperatures as high as 46° C. have been reported. Leakage of myoglobin into the blood as a result of membrane damage may trigger kidney failure in survivors. Some survivors never regain consciousness and others have central nervous system damage (e.g. paralysis, blindness, deafness, impaired intelligence, speech defects) as a result of extremely high fever and/or electrolyte imbalance [Steward D. J. and O'Connor, G. A. R. supra, (1987)].

Accurate laboratory tests are required which can detect individuals at risk for developing malignant hyperthermia. Currently, the best test for individuals at risk is a diagnostic muscle biopsy. This test, described by Kalow et al. ["Metabolic error of muscle metabolism after recovery from malignant hyperthermia", *Lancet*, 2: 895–898, (1970)], is based on the abnormal contracture response of MH muscle to caffeine, halothane and a combination of the two. It is a highly invasive procedure, requiring 10–15 grams of thigh muscle. Moreover the tests are time-consuming and sometimes inconclusive. The concordance between tests is poor such that an individual may be labelled "at risk" by the criteria of one test and "not at risk" by the criteria of a second. Other individuals may be equivocal due to overlap in the values for "at risk" and "not at risk" groups. Control values and diagnostic "cut-off" points have to be established in each laboratory so that it is difficult to establish new units to test for MH susceptibility. Moreover, such an invasive technique is inappropriate for general population screening prior to anaesthesia. Thus, the availability of a DNA based diagnostic test is of major significance and utility for detection of individuals at risk for malignant hyperthermia.

Porcine halothane sensitivity represents an excellent animal model for malignant hyperthermia. The clinical crisis in pigs follows a very similar course to that in humans and crises may be similarly arrested or averted by prompt treatment with dantrolene sodium. In pigs, however, the syndrome may additionally be triggered by over-exercise and/or stress. Usually over-exercise is not a significant problem in the raising of pigs. However, stress is a problem as particularly experienced during shipping and prior to slaughter. The pig industry loses hundreds of thousands of dollars a year due to deaths or spoiled meat caused by pigs being susceptible to malignant hyperthermia.

While it has been described as a recessive condition in pigs, it is more likely to be a co-dominant condition since muscle biopsy studies [Britt, B. A., et al, "Malignant Hyperthermia—pattern of inheritance in Swine". In Aldrete J. A. eds., Second International Symposium on Malignant Hyperthermia. New York, Grune and Stratton, pp 195–211, (1978)] reveal that heterozygous pigs may be mildly affected and homozygous MH/MH pigs may be more seriously affected.

The gene responsible for halothane sensitivity (HAL) has been found to segregate in pigs with a number of other genetic markers including S (S Locus affecting expression of A-O red blood antigens), Phi (glucose phosphate isomerase), H (H locus encoding blood group antigens), Po2 (postalbumin-2) and PgD (6-phospho-gluconate dehydrogenase), [Archibald, A. L. and Imlah, P., *Animal Blood Groups and Biochem. Genet.* 16: 253–263, (1985)]. It is therefore assumed that these genes are linked on one pig chromosome. Since genetic linkage groups are often conserved throughout the animal kingdom and since the human equivalents of three of these genetic markers (Phi, Po2 and H) have been found to map to human chromosome 19 [Shaw, D. and Eiberg, H., Report of the Committee for chromosomes 17, 18, and 19. Human Gene Mapping 9 (1987); Ninth International Workshop on Human Gene Mapping. *Cytogenet. Cell Genet,* vol 46, Nos. 1-4, (1987)],. there was reason to suggest that the human gene for MH may also be in this gene cluster on chromosome 19. A possible further localization of MH to the long arm (q) of chromosome 19 was suggested by the fact that the H gene analog maps to 19q and the Phi gene analog (GPI) maps to band 19q12-19q13 on 19q (Shaw and Eiberg, supra).

In recent years it has been possible to track genetic disease genes in families using closely linked genetic markers. The most commonly used marker of a chromosome site is a restriction enzyme cleavage site that may be present (+) on the pair of chromosomes in some members of the population or absent (−) at the same site in the chromosome pair of other members of the population. Still other individuals will be heterozygous (±) having one chromosome of each type [Botstein, E. et al, *Am. J. Hum. Genet.* 32: 314–331, (1980)]. The (+) chromosome can be distinguished from the (−) chromosome by extracting DNA from the blood cells (or other cells) of the test individual, treating it with the restriction enzyme whose cleavage site is "polymorphic" (i.e. cleaves or doesn't cleave) and fractionating the DNA fragments by size. The DNA from a chromosome without the cleavage site gives a larger fragment than the DNA from a chromosome with the cleavage site, providing an assay for the presence or absence of the cleavage site. The term RFLP is an acronym for restriction fragment length polymorphism. An RFLP constitutes a genetic marker allowing the polymorphic chromosome site to be tracked in a family. Any genetic disease that tracks (segregates) in a family with the RFLP marker is considered to be linked to the marker, that is it maps near to the marker on the chromosome which they share.

SUMMARY OF THE INVENTION

According to an aspect of the invention, substantially purified DNA sequence encoding for human ryanodine receptor and its functional equivalents is characterized by:
  i) the DNA encoding for a protein having 5032 amino acids and a molecular weight of approxmately 563,000 daltons;
  ii) the DNA having a length of approximately 15.3 kb; and
  iii) isolated from chromosome 19 of humans.

According to another aspect of the process, substantially purified cDNA has the sequence encoding for the amino acid positions 1 to 5032 of FIG. 2.

According to another aspect of the invention, a DNA probe includes a fragment of the DNA encoding for the human ryanodine receptor protein.

According to a further aspect of the invention, the use of the DNA probe in RFLP analysis determines if a subject is susceptible to malignant hyperthermia.

According to another aspect of the invention, substantially purified ryanodine receptor protein is free of any foreign human protein. The protein has a molecular weight of approximately 563,000 daltons and an amino acid sequence of FIG. 2.

According to another aspect of the invention, substantially purified antibodies specific to a protein fragment of the human ryanodine receptor protein is disclosed. The antibodies may be either polyclonal antibodies or monoclonal antibodies. Such antibodies may be used in an amino acid assay to determine if a human or animal is susceptible to malignant hyperthermia.

BRIEF DESCRIPTION OF THE DRAWINGS

Preferred embodiments of the invention are discussed with respect to the drawings, wherein;

FIGS. 2A to 2A-12 is the nucleotide sequence (upper row) and deduced amino acid sequence (lower row) of the human ryanodine receptor cDNA. Sequences underlined once correspond to peptide sequences determined from the purified receptor protein. Sequences underlined twice are potential phosphorylation sites.

FIGS. 5A–B is a Restriction Fragment Length Polymorphism (RFLP) analysis of two representative malignant hyperthermia families.

DETAILED DESCRIPTION OF THE PREFERRED EMBODIMENTS

Figure 1:
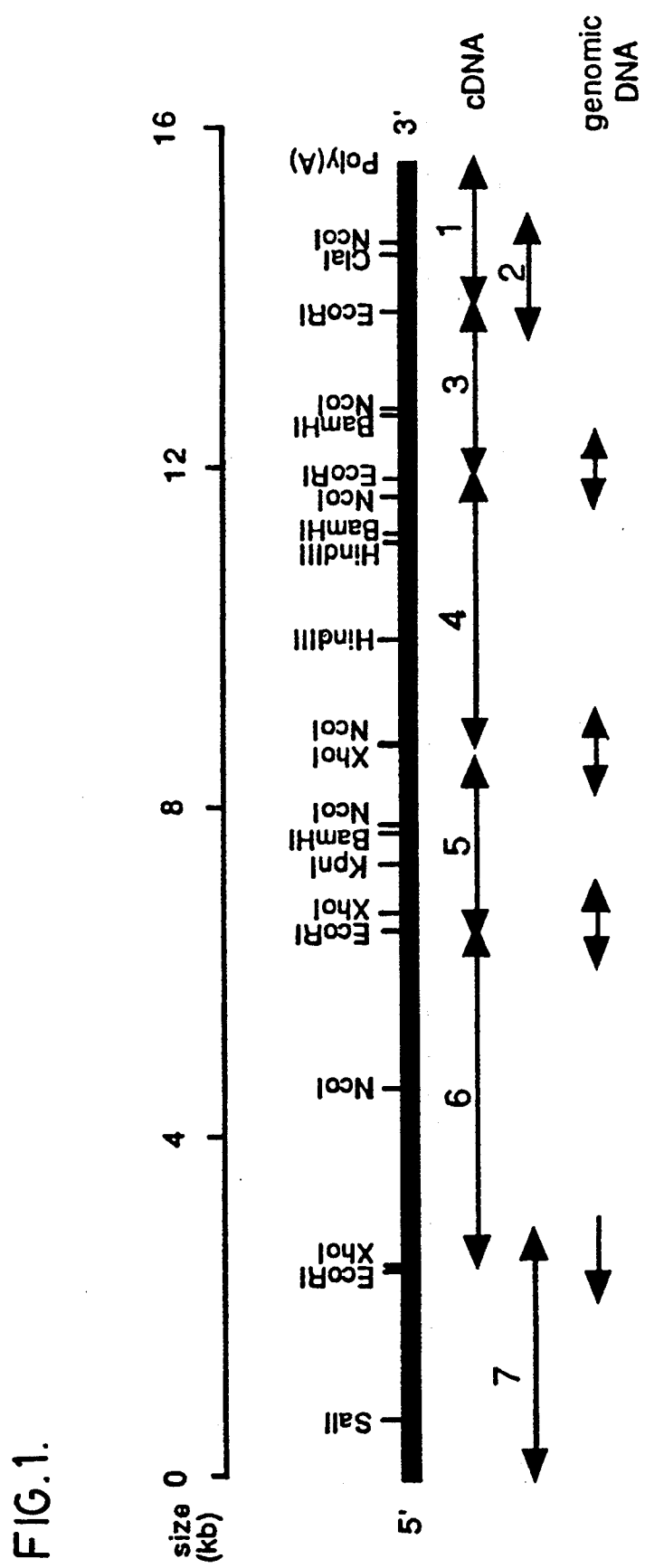
FIG. 1 is a schematic drawing showing the restriction endonuclease map and sequencing strategy of the human ryanodine receptor (HRR).

The sustained muscle contraction in MH suggests that the problem in this disease may be related to the release of calcium into the muscle cell cytoplasm from the sarcoplasmic reticulum (SR). The calcium release channel in muscle is a large protein that spans the gap between a membranous structure called the transverse tubule and the SR. Recently evidence has been accumulated to show that this protein is equivalent to the "ryanodine receptor" protein and researchers have speculated that a defect in the channel might be the basic defect in animals, including humans, with MH.

This invention shows that the ryanodine receptor gene is the gene that is defective in MH. This application discloses isolation of the gene that encodes the human ryanodine receptor protein, mapping of the human ryanodine receptor (HER) gene to human chromosome 19, further mapping the MH gene to the long arm of chromosome 19 and determination that RFLP markers within the HRR gene segregate 100% of the time with the MH phenotype. The HRR gene is believed to be the gene responsible for MH and DNA probes from the HRR gene constitute the basis for a definitive diagnostic test for MH.

The primary defect in MH is believed to be in calcium regulation. Myoplasmic calcium rises rapidly during onset of MH in MH susceptible pigs, and this is rapidly reversed by administration of dantrolene [Lopez, J. R., Allen, P., Alamo, L., Jones D., and Sreter F. *Muscle Nerve,* 11, 82–88, (1988)]. While the calcium-ATPase protein (Calcium pump) appears to function normally in both human and pig MH muscle, several studies indicated a defect in the calcium induced calcium release channel.

The resting level of calcium is elevated in the myoplasm of MH muscle while other reports indicate that calcium induced calcium release is activated at a lower calcium threshold in heavy SR isolated from MH pigs than in heavy SR isolated from normal pigs and that this threshold is further lowered in the presence of halothane. Ohta, T, Endo, M, Nakano, T., Morohoshi, Y, Wanikawa K, Ohga, A, *American Physiological society* C358–367, (1989) reported that muscle from MH sensitive (MHS) pigs has a significantly higher rate of calcium induced calcium release than normal. Mickelson et al (*J. Biol. Chem.* 264: 1715–1722, 1988) also showed an increased rate of calcium induced calcium release in MHS muscle.

The calcium release channel in muscle is a large protein that spans the gap between the transverse tubule and the SR. The channel is activated by calcium, caffeine, halothane, and micro-molar ryanodine, and inhibited by ruthenium red, tetracains, calmodulin, high $Mg^{2+}$ and mM ryanodine [Lai F. A. et al, *Nature,* 331: 315–319, (1988)]. The resting level of calcium is elevated in the myoplasm of MH muscle (Lopez et al, supra), and calcium-induced calcium release is activated at a lower calcium threshold in MH pigs than in normal pigs. This threshold is further lowered in the presence of halothane (Nelson, 1988). Ohta et al supra, and Mickelson et al. supra, both reported an increased rate of calcium induced calcium release in MHS muscle. The latter study indicated that the ryanodine receptor from MHS muscle has a higher affinity for ryanodine binding and requires higher concentrations of calcium to inhibit ryanodine binding.

Ryanodine causes contracture of skeletal muscle in vitro in both pig and human, similar to that induced by caffeine and/or halothane and reportedly discriminates more effectively between MH and normal muscle.

The rabbit ryanodine receptor has recently been cloned [Takeshima, H. et al., *Nature,* 339: 439–445, (1989)] independently of the work disclosed herein. The deduced amino acid sequence comprises 5037 amino acids. The predicted protein structure suggests that the calcium release channel, comprising four transmembrane domains and potential regulatory sequences, lies in the C-terminal portion of the molecule. The remainder of the protein is predicted to constitute the "foot" portion which spans the gap between the transverse tubule and the SR.

The C-terminal fifth of the predicted structure of the human ryanodine receptor contains from four to ten transmembrane segments which form the channel itself. Potential binding sites for calcium, calmodulin, ATP and other modulators of calcium channel function are also believed to be present in the molecule. Two of these transmembrane regions show limited homology to transmembrane regions of the nicotinic acetylcholine receptor (nAChR). Specific amino acid substitutions which alter the charge distribution in the Torpedo nAChR have been shown to alter channel conductance [Imota, K. et al *Nature,* 335: 645–648, (1988)]. By analogy, amino acid substitutions in the homologous transmembrane segments of the human ryanodine receptor could alter rates of calcium release and account for the MH phenotype.

The initial rabbit cDNA clones were obtained by screening a λgt11 expression cDNA library with affinity purified polyclonal antibody directed against epitopes on the purified rabbit ryanodine receptor protein as described in [Zorzato, F., et al, *Biochem. J.* 261: 863–870, (1989)]. The protein sequence is published in Takeshima et al (supra) and hence readily available to the public. Two initial rabbit cDNA clones were isolated from this library. Restriction endonuclease fragments from these clones were then used as probes to isolate longer cDNA clones from a neonatal rabbit skeletal muscle cDNA library. This library is freely available and is described in MacLennan, D. H., et al, *Nature* 316: 696–700 (1985). All the libraries used in this application are freely available. It is understood by those skilled in the art, however, that any library prepared from skeletal muscle according to established methods should be representative of the RNA species present in the tissue, and can therefore potentially be the source of a ryanodine receptor clone.

Further extension of the clones was achieved by the use of a primer extension library using neonatal rabbit muscle poly A+RNA.

The rabbit ryanodine receptor cDNA probes were used to isolate the HRR cDNA on the basis of cross-species conservation. A series of six linear clones were isolated from a human skeletal muscle cDNA library in λgt10. These clones are presented in FIG. 1, labelled as cDNA 1 through 6. cDNA clone. 7 in FIG. 1 was isolated from a primer extension library constructed from human skeletal muscle mRNA.

Genomic DNA spanning the non-overlapping cDNA fragments shown in FIG. 1 was isolated from a chromosome 19 specific library, designation Lawrence Livermore LL19NL01 Human Chromosome 19 Library in Charon 4A by the American Type Culture Collection, Rockville, Md.

FIG. 1 presents the restriction map and sequencing strategy for the human ryanodine receptor cDNA. The first line shows the size in kb of the full length cDNA. The second shows a partial restriction endonuclease map of the 15.3 kb cDNA which encodes the human ryanodine receptor protein. The third and fourth lines define the 6 cDNA clones (1–6) that were isolated from the first cDNA library and the single clone (7) that was isolated from a primer extended human cDNA library. Arrows inside the clones indicate that they were all sequenced in two directions. The fifth line designates the regions where genomic DNAs were sequenced to obtain overlapping sequences between the various clones. HRR probes 1,2,3,4,5, and 6 described in this application, correspond to cDNA clones 1,3,4,5,6 and 7, respectively.

FIGS. 2A—2A-12 presents the nucleotide and deduced amino acid sequences of the cDNA encoding the human ryanodine receptor. The nucleotide are numbered positively beginning at the first residue of the initiator methionine codon. The nucleotide comprising the 5′ non translated region are numbered negatively in the 3′ to 5′ orientation. The deduced amino acid sequence of the open reading frame is numbered from 1 to 5032. Peptide sequences determined from the purified receptor are underlined once. The potential phosphorylation sites are underlined twice. The 3' untranslated region, beginning after the TGA termination codon, is 142 bp long. A canonical AAAATAAA polyadenylation signal [Proudfoot, N. J. and Brownlee, G. G., Nature 263: 211–214, (1976)] is found 19 bases upstream of the polyadenylation site and this is followed closely by the TG-rich sequence TCTGTCGTACG, characteristic of sequences between the polyadenylation signal and the polyadenylation site [McLauchlan, J. et al., Nucleic Acids Res. 13: 1347–1368, (1985)]. The initiator methionine is 15096 bp upstream of the termination codon. The initiator methionine codon is present in the longer sequence ACATCATGG which closely resembles the consensus initiation sequence, CCA(G)CCATGG [Kozak, M, Nature 308: 241–246, (1984)]. The human cDNA sequence of FIG. 2 encodes a protein of 5032 amino acids with a predicted molecular weight of 563,584. It is understood that the term substantially pure as used herein means that the isolated and purified DNA or protein is free of any foreign animal DNA or protein. It is also understood that, with reference to disclosed and claimed DNA or protein sequences, various functional equivalents exist which are due to substitutions in variable regions of the DNA sequence or protein which does not affect the essential function of the DNA sequence or protein sequence.

Proof that the cDNA coded for the ryanodine receptor gene was provided by several lines of evidence. The fusion protein expressed by the clones reacted with a second antibody raised against the purified 30S ryanodine receptor [Meissner, G. Rousseau, E. and Lai, F. A. J. Biol. Chem. 264: 1715–1722, (1989)]. As further evidence, both rabbit and human probes from the coding region of the cDNA hybridized to a message of approximately 15 kb in rabbit muscle mRNA. Tryptic peptides prepared from the rabbit ryanodine receptor were sequenced. The primer extension and DNA sequence analysis of the cDNA clones revealed four deduced amino acid sequences corresponding to the sequences of the tryptic peptides derived from the purified ryanodine receptor protein. These sequences are underlined in FIG. 2. Further evidence that the clones encoded the ryanodine receptor is provided by noting that the deduced amino acid sequence would give rise to a protein with several transmembrane passages only in the carboxyl-terminal fifth of the molecule and that the bulk of the protein was hydrophilic. Such a predicted protein would match very well with the structure of the ryanodine receptor in which the bulk of the protein is cytoplasmic and only a small segment is transmembrane [Wagenknecht, T. et al., Nature 338: 167–170, (1989)].

Figure 3:
FIG. 3 is a Southern blot hybridization using human-rodent somatic cell hybrids to localize the gene to human chromosome 19.

Localization of the ryanodine receptor gene on human chromosome 19 was determined using a panel of 55 human-rodent somatic cell hybrids [MacLennan, D. H. et al., Somat. Cell and Mol. Genet. 13: 341–346, (1987)]. FIG. 3 shows filter hybridization analysis of the human ryanodine receptor gene. DNAs are from human (lane 1), mouse (lane 2) and mouse-human hybrids (lanes 3 and 4) (MacLennan et al supra). DNAs were digested with EcoR1 and Southern blot analysis was performed with the probe pHRR-XH-1, a 1001 bp Xho1-Hind III fragment from the human ryanodine receptor cDNA, consisting of bases 8550 to 9550 in the human cDNA sequence (FIG. 2). The hybrid in lane 3 contained human chromosome 19; the hybrid in lane 4 did not. The presence or absence of chromosome 19 in the 13 somatic cell hybrids used in this study was confirmed both cytogenetically and with DNA probes from chromosome 19. The 15 kb EcoR1 band in human genomic DNA hybridizes to the probe pHRR-XH-1. Cross hybridization to mouse bands at 2.4, 2.1 and 0.5 kb was also observed. Analysis of a series of 13 somatic cell hybrids revealed 100% concordance for the presence of chromosome 19 and the presence of a 15 kb EcoR1 restriction fragment which hybridized to the human ryanodine receptor probe pHRR-XH-1 as shown in FIG. 3. As shown in Table 1, for all other chromosomes, including X and Y chromosomes, discordance ranged from 23% to 77%.

TABLE 1

Chromosome Mapping of Human Ryanodine Receptor Gene

| Chromosome No. | Discordant | Discordancy (%) |
| --- | --- | --- |
| 1 | 3 | 23 |
| 2 | 4 | 31 |
| 3 | 6 | 46 |
| 4 | 9 | 69 |
| 5 | 8 | 62 |
| 6 | 5 | 38 |
| 7 | 5 | 42 |
| 8 | 5 | 38 |
| 9 | 5 | 38 |
| 10 | 5 | 38 |
| 11 | 5 | 38 |
| 12 | 5 | 38 |
| 13 | 9 | 69 |
| 14 | 6 | 46 |
| 15 | 6 | 46 |
| 16 | 4 | 31 |
| 17 | 7 | 54 |
| 18 | 5 | 38 |
| 19 | 0 | 0 |
| 20 | 7 | 54 |
| 21 | 6 | 46 |
| 22 | 10 | 77 |
| X | 7 | 54 |
| Y | 6 | 46 |

Figure 4:
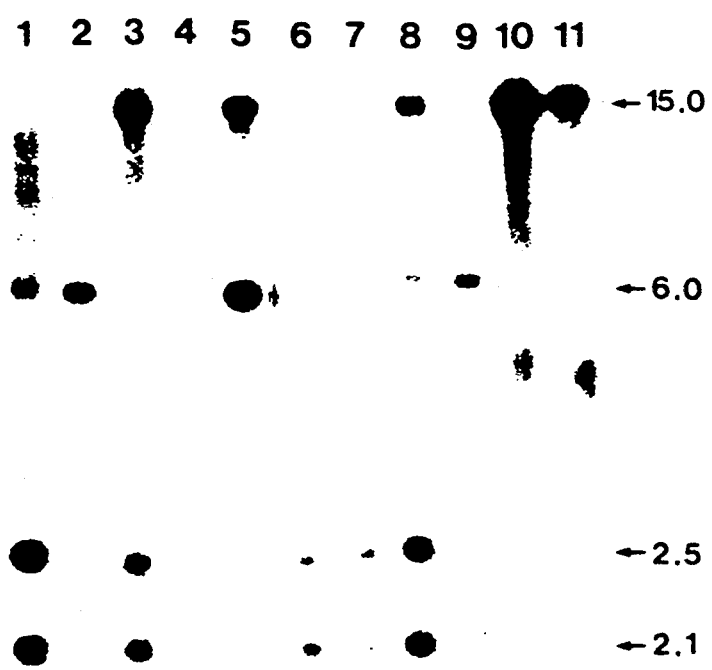
FIG. 4 is a Southern blot hybridization using somatic cell hybrids derived from chromosome 19 reciprocal translocation, to further localize the ryanodine receptor gene on human chromosome 19.

Chromosome 19 regional sublocalization of the gene identified by the probe pHRR-XH-1 was accomplished using a panel of somatic cell hybrids that were derived from a variety of reciprocal translocations involving human chromosome 19. The construction and analysis of these hybrids have been described by Brook, I. D. et al., Hum. Genet. 68: 282–285, (1984), Bufton, L. et al., Am. J. Hum. Genet. 38: 447–460, (1986), Korneluk, R. G. et al., Genomis in press, (1989); Lusis A. J. et al., Proc. Nat. Acad. Sci,. U.S.A. 83: 3929–3933, (1986); Mohandas T. et al., Proc. Nat. Acad. Sci. U.S.A. 77: 6759–6763, (1980). FIG. 4 shows genomic DNA extracted from hybrid and control cells, digested to completion with Eco R1 and separated by electrophoresis for subsequent Southern blot analysis. The autoradiograph depicts the hybridization pattern of the probe pHRR-XH-1 to DNA extracted from (1) Mouse A9 control; (2) Hamster E36 control; (3) G24A9 (retains 19p13→19qter); (4) G24B2TG (back selected for the loss of 19p13→19qter); (5) G35E4 (contains 19 pter→19q13.3); (6) B-9 (has 19q13.2→19qter); (7) GM89A99C7B (retains 19q13.3→19qter); (8) CF104-19/6 (has 19 cen→qter); (9) G89E5 (contains a normal human X chromosome only); (10) normal human male; (11) normal human female. The EcoR1 fragment from human chromosome 19 which hybridizes with probe pHRR-XH-1 is approximately 15 kb in size. Cross-hybridization of the probe pHRR-XH-1 to hamster DNA sequences is seen at 6.0 kb and to mouse EcoR1 fragments at 2.4 and 2.1 kb. FIG. 4 illustrates that the HRR probe hybridizes to genomic digests of human DNA from hybrids that retain the proximal 19q region; p13→qter (lane 3), pter→q13.3 (lane 5) and cen→qter (lane 8). By contrast, hybrids that contain the distal 19q regions q13.2→qter (lane 6) and q13.3→qter (lane 7) did not show binding to the probe pHRR-XH-1. These results sublocalize the HER probe to the proximal 19q region in the interval cen→q13.2.

To demonstrate that the HRR gene is the gene that, when mutated, is the cause of MH, RFLP markers that are part of the HRR gene have been found to segregate with the MH gene (and therefore the MH phenotype) in families. To show this, blood samples from members of several MH families were obtained and subjected to RFLP analysis. The RFLPs examined included several previously reported genetic markers that had been mapped to chromosome 19. More importantly several new RFLPs are described that are recognized by cDNA probes from the HRR gene, thereby establishing the means to test the HRR gene directly for co-segregation with the MH phenotype.

RFLPs in the HRR gene were identified by using various cDNA clones from the HRR gene as probes to detect hybridizing sequences on Southern blots of DNA from a set of normal individuals. Samples of the test DNA were cleaved with each of several restriction enzymes, the fragments were size fractionated by electrophoresis in agarose gels and blotted to a nylon membrane. Denatured DNA on the membrane was hybridized by standard procedures with 32P labelled HRR cDNA probes, and the position of hybridizing sequences was determined by standard autoradiographic procedures. Any probe/enzyme combination that revealed a variation in fragment size among the tested individuals defined a new RFLP.

In total, eleven RFLPs were defined in the HRR gene. Their properties are summarized in Table 2. For each RFLP found the HRR cDNA probe is listed in column 1, the restriction enzyme with the polymorphic site is listed in column 2, the variable fragment sizes (alleles) are provided in column 3, constant size fragments in column 4, and the frequencies of the alleles are provided in column 5.

TABLE 2

Human Ryanodine Receptor Probe Information

| Probe | Polymorphic Enzyme | Polymorphic Fragment Sizes (Alleles) | Constant Bands | Allele Frequencies |
|---|---|---|---|---|
| HRR1-600 | Ban I | 6.0/13/0 | | .22/.78 |
| HRR3-1000 | Hind III | 19.0/22. | | .04/.96 |
| | PVU II* | 6.5/4.4/1.9 | | .25/.75 |
| | Ban HI* | 19.0/14.0,5.0 | | .75/.25 |
| HRR3-1200 | Pvu II | 1.9,3.9/5.8 | | .11/.89 |
| HRR4-2400 | Taq I | 1.8/1.1,0.7 | 3.5 | .20/.80 |
| | Bcl I | 11.5/8.4,2.9 | 4.6,3.0 | .78/.22 |
| | EcoRV | 28.0/2.5 | 11.0 | |
| HRR5-3800 | Eco RI | 24.0/16.0,9.0 | | .14/.86 |
| | Taq I | 1.9/1.6,0.3 | | |
| | Msp I | 1.8/2.2 | | |

*Pvu and Bam HI polymorphisms are in total linkage disequilibrium with each other, and were treated as a single genetic marker.

These probes can be defined more particularly by reference to the nucleotide sequence of FIG. 2. HRR 1-1600 is an approximately 1.6 kb fragment spanning nucleotides 13602 to 15243 shown in FIG. 2. HRR 2-2000 is an approximately 2 kb fragment spanning nucleotides 11613 to 13607 in FIG. 2. HRR 3-3100 is an approximately 3.1 kb fragment spanning nucleotides 8515–11618 shown in FIG. 2. HRR 3-1000 is a subfragment of HRR 3-3100, of approximately 1 kb, spanning nucleotides 8515–9554 shown in FIG. 2. HRR 3-1200 is also a subfragment of HRR 3-3100, of approximately 1.2 kb, spanning nucleotides 9549–10851 shown in FIG. 2. HRR 4-2400 is an approximately 2.4 kb fragment spanning nucleotides 6125–8493 shown in FIG. 2. HRR 5-3800 is an approximately 3.8 kb fragment spanning nucleotides 2391–6125 shown in FIG. 2. In addition, HRR 7A (nucleotides 186–2396) and 7B (nucleotides 104–548) have been tested, but have not revealed any RFLP markers with the restriction enzymes tested.

With this set of HRR gene markers, it was possible to test for segregation of the markers with the MH phenotype in MH families. Families selected for study had been under investigation for many years at the Toronto General Hospital. Families chosen were those with a potential for at least two informative offspring, (is ones in which the MH gene has been inherited from an affected parent who is heterozygous for both the MH gene [one normal and one mutant allele] and the genetic marker at the HRR gene [one allele of each type]). Family members were classified as affected if they had either an MH reaction or muscle biopsy results which were unequivocally affected. In some cases the status of the second parent had to be inferred as only one parent had been biopsied. Muscle biopsies were performed according to the North American Malignant Hyperthermia protocol (Britt, 1988) as described below. Biopsy test results were considered to be unequivocal if at least two parameters were consistent, not being intermediate and/or ambiguous.

Three muscle biopsy drug tests were performed on separate muscle strips—halothane, caffeine, and caffeine plus halothane. These tests are all based on the different contracture responsiveness of normal and Malignant Hyperthermia affected muscle (Table 3).

TABLE 3

| Muscle Biopsy Test Criteria (age > 10 Years) | | |
|---|---|---|
| | Normal | Affected |
| Halothane | | |
| 1% | <0.2 g | >0.3 g |
| 3% | <0.7 g | >0.8 g |
| Caffeine | >4.0 mM | <4.0 mM |
| Caff. + Hal. | >0.5 mM | <0.35 mM |

Caffeine - added cumulativele (1,2,4,8,16,32 Mm) measure contracture - baseline to plateau
Caff + Hal. - caffeine added muculatively (0.25,0.5,1,2,4,8,16,32) after 10 min in 1% halothane Muscle biopsies were taken from affected individuals and their first degree relatives with a requirement for a lean body mass of 20 kilograms. At least two to three months was left between an MH reaction and the diagnostic biopsy. Surgery was performed using nitrous oxide, Innovar and midazolam. No dantrolene was administered prior to surgery as this can alter test results. The muscles chosen for biopsy were the vastus lateralis, rectis abdominis, or gracilis. These three muscles all react similarly in the caffeine halothane contracture test.

Good twitch viability in each specimen was demonstrated prior to testing. A 20 minute period was allowed in order to establish stable twitch heights and baselines prior to addition of drugs. 1% halothane contracture tests were performed on all individuals. 3% halothane testing was done on some individuals. In each case exposure time was 10 minutes. The amplitude of the contractures was measured and a contracture of greater than 0.3 g at 1% and 0.7 g at 3% was defined as abnormal. For the caffeine test, caffeine is added incrementally at 4 minute intervals from 0.5 mM doubling to 32 mM. Contractures in response to each dose were measured four minutes after each addition of drug. The dose of caffeine required to raise the resting tension by 1 g (Caffeine Specific Concentration) was calculated. Values greater than 4 mM were considered normal. In the caffeine plus halothane test, muscle strips were equilibrated for 15 minutes with 1% halothane. Caffeine was then added incrementally from 0.25 mM doubling to 32 mM and the Caffeine Specific Concentration in the presence of Halothane was calculated similarly. Values greater than 0.5 mM were considered to be normal. Individuals with values less than 0.35 mM were considered to be affected. Table 3 lists the test criteria that were used to determine whether a result was positive or negative. In general the caffeine plus halothane test was taken as the most definitive and in most instances the caffeine test was in agreement with this. The halothane test (with 1% halothane) tended to give false negatives and it was ignored if the two other tests were positive. To avoid possible confusion, families with discrepant results or families that did not fit the standard criteria for autosomal dominant inheritance were not used for RFLP analysis. On this basis 19 families were chosen for study.

Two examples of typical families are presented in FIGS. 5a and 5b, in which the following symbols are employed:
R=REACTION
H=+veHALOTHANE
C=+veCAFFEINE
K=+veCAFF.+HAL.
PN=PRESYM. NORM
N=NORMAL TESTS. In FIG. 5a, data are presented for family 5. The mother has had a reaction (R) and also scores positive for the caffeine plus halothane test (K). Her husband is presumed to be normal. Three children are affected according to the biopsy results. Segregation was examined for three HRR gene RFLPs, two of them recognized by HRR3 and one by HRR4. There is one constant band (C). The three pairs of polymorphic fragments are 22 and 19 kb (HRR3 with HindIII—table 1), 11.5 and 8.4 kb (HRR4 with BclI—a 2.9 kb fragment that goes with the 8.4 kb fragment is not shown—table 1) and 6.5 and 4.4 kb (HRR3 with PvuII—a 1.9 kb fragment that goes with the 4.4 kb fragment is not shown—table 1). For each of the RFLP markers the father is homozygous for one allele and the mother is heterozygous for the two alleles. In the case of the first RFLP, for example, the father has 22/22 and the mother has 22/19. All three affected children received the 22 kb marker from both parents. Thus all three received the 22 kb allele from mother along with the MH gene they also received from her. While this could occur by chance it is consistent with the MH gene and the HRR gene segregating together due to close linkage or identity of the two genes. The same reasoning applies to the other two RFLPs that were informative in this family.

FIG. 5b, shows Family 12, in which the father and two offspring are affected. Two RFLPs were examined, one with a constant size fragment (C) and alleles of 6.5 and 4.4 kb (as in FIG. 5a) and one detected with a probe from the ApoCII gene (Shaw and Eiberg, supra) that maps close to the HRR gene on chromosome 19. The latter detects alleles of 3.8 and 3.5 kb. For the HRR3 RFLP father is heterozygous 6.5/4.4 and mother is homozygous 4.4/4.4. All four offspring must have received a 4.4 kb allele from mother. The two normal girls received 4.4 from father while the two affected individuals received the 6.5 kb allele from him. This could have occurred by chance but it is also consistent with the 6.5 kb allele segregating with the mutant MH gene on one chromosome 19 and the 4.4 kb allele segregating with the normal MH gene on the other chromosome 19. A Similar result is obtained for the ApoCII genetic marker with the two normal girls receiving the opposite ApoCII alleles from their affected siblings. This is consistent with linkage of the ApoCII gene with the MH gene but could also be a chance occurrence.

These two representative families illustrate that the genetic test for linkage of chromosome markers with the MH gene is a statistical one. In any family the segregation pattern could always occur by chance or by co-segregation of the two markers with the disease due to true genetic linkage. To demonstrate that linkage is more likely than chance occurrence requires that several families be examined and that a statistical analysis be performed. Table 4 summarizes the data from 19 families examined. Eight families gave informative results with one or more of the HRR gene probes, with results obtained on 19 offspring of affected parents. In every family the affected children all received the same HRR marker and the unaffected ones all received the alternate form. The probability of this occurring by chance is small. Standard linkage analysis was performed to determine the odds of this result being due to linkage rather than chance. The results are as shown in Table 4.

TABLE 4

| MH GENE AND HRR-GENE LINKAGE | |
|---|---|
| Linkage Dist. (CM) | LOD Score |
| 0.00 | 3.31 |
| 0.01 | 3.22 |
| 0.02 | 3.15 |
| 0.05 | 2.91 |
| 0.10 | 2.51 |
| 0.20 | 1.71 |
| 0.40 | 0.30 |

The tabulated values are the log of the odds (to base 10) otherwise known as the LOD score. Performing this calculation for different possible presumed distances between the HRR gene and the MH gene demonstrates that the highest odds are attained at a presumed distance of zero. This suggests that the most likely interpretation is that the two genes are the same. Since three is the log of 1000, a LOD score of greater than three indicates that the odds in favor of linkage versus chance are greater than 1000 to 1. It is reasonable to conclude that the HRR gene is in fact the gene that, when mutated, is the cause of MH. This conclusion is strengthened by the fact that among eight additional families who are not informative for the HRR gene probes, but were informative for genetic markers that flank the HRR gene on chromosome 19, only three recombination events were detected between the MH gene and the flanking marker. This also provides definitive evidence that the MH gene maps to the same region of the chromosome as the HRR gene.

RFLP markers detected by HRR cDNA clones segregated 100% of the time with the MH phenotype in families informative with these probes. Given that all the relevant family members are available for DNA testing, it can be possible to determine the MH status of family members who have not had an MH reaction or a muscle biopsy. Both the affected individual and his or her parents or siblings whose MH status is known must be available. For example, if a parent and child are affected, determining the status of the other children in the family would be possible if both parents and the affected child are available for DNA testing. In another example, it is possible to diagnose the first offspring in a family where both a parent and grandparent are known to be affected. In this case, it would be necessary to have both parents and grandparents as well as the child to study. At present the test requires that one of the eleven markers previously defined be informative in a family for the diagnosis to be made. Eight of the nineteen families used to establish the LOD score fit these criteria.

Markers which flank the HRR gene may also be used to track the disease but the risk of a recombination event (which uncouples the markers from the disease phenotype) will increase with distance from the MH gene and result in the misdiagnosis rate of a few percent. New markers can be developed by screening genomic clones detected by the HRR cDNA for multiple copies of dinucleotide repeats. Such markers are analysed by the polymerase chain reaction (PCR) and have multiple alleles in the population [Weber, J. L. and May, P. E. *Am. J. Hum. Genet.* 44: 338-396, (1989)]. These can provide intragenic probes informative in a greater proportion of families and thus avoid the need for flanking markers with their associated risk of recombination with the disease phenotype.

Analysis of current linkage data does not indicate the existence of a common haplotype(s) associated with human MH which indicates that multiple mutations of the MH gene may be found. In order to develop a test for general population screening, it will be necessary to find and characterize each mutation.

Knowledge of the normal HRR cDNA sequence disclosed herein allows amplification of segment cDNA copies of the normal and mutated genes using the polymerase chain reaction. Mutations will be apparent as sequence discrepancies (with respect to the cloned DNA sequence) in the heterozygous state (for direct sequencing) or in the hemizygous state (for cloned sequence). By using cDNA, RNA processing mutations will be detected in addition to base substitutions, deletions, duplications, or insertions.

Once a mutation is defined, oligonucleotides, derived from the normal sequence may be synthesized which flank the mutation and can be used to amplify both normal and mutant alleles. Short oligonucleotides containing either the mutated region of the HRR gene or the corresponding normal site of the HRR gene should then be synthesized and used as probes, in turn, to test blots of amplified DNA containing the region of interest. The mutant sequence oligonucleotide should hybridize only to DNA from affected individuals, whereas the normal sequence oligonucleotide should hybridize to DNA from both affected and unaffected individuals. It should also be possible to design an allele specific oligonucleotide based on the sequence of a mutation(s), which in conjunction with a normal HRR sequence oligonucleotide will, in a PCR reaction, generate product only in affected individuals.

To confirm that potential discrepancies represent a mutation, rather than a polymorphism, each such sequencing discrepancy must be examined in both normal and affected individuals by means of restriction enzyme analysis (if the mutation creates or destroys a site), by allele specific amplification, by differential oligonucleotide hybridization, Chemical cleavage [Cotton et al, *Proc, Nat. Acad. Sci. U.S.A.,* 85: 4397-4401, (1985)], denaturing gradient gel electrophoresis [Myers and Maniatis, *Cold Spring Harbour Symp. Quant. Biol.* 51: 275-284, (1986)], RNase protection [Myers, R. M., Larin, J., and T. Maniatis, *Science* 230: 1242, (1985)], or by DNA sequencing, as appropriate. A discrepancy which would alter the amino acid constitution of the HRR protein and which occurs in several affected individuals, but never in normals, would almost certainly represent a mutation. Alternative explanations such as segregation of a polymorphic marker closely linked to the mutation are unlikely, given that common MH haplotypes have not been observed. Once mutations are confirmed, further diagnostic tests may be developed.

DNA sequencing of genomic clones can be performed to determine intron-exon boundaries for the HRR gene. As these are established, it becomes possible to amplify from DNA rather than cDNA, enabling investigation on patients for whom muscle biopsy samples are not available and to expand the study to include additional patients as each mutation is defined. Such an application would also allow one to detect mutations in introns or at intron/exon borders that affect splicing of the message and lead to aberrant protein which would only be inferred from a cDNA based analysis.

The ease of developing a general diagnostic test for MH is dependent on the number of mutations in the gene that cause the MH phenotype. As each mutation is traced a test may be developed which may be informative in all individuals in the family in which it was found and for others which share the mutation. Common mutations may be screened for amongst patients presenting for diagnostic biopsy and once a mutation or mutations comprising a cost and time effective proportion of MH individuals are described, a general population test can be developed.

The type of genetic analysis using RFLPs in humans herein described can also be applied to pigs. Cross species hybridization allows the direct detection of pig RFLPs with the human cDNA. RFLP's detected by the porcine GPI cDNA and GPI gene, closely linked to Hal (MH) have been successfully used in this type of analysis [Davies, W. et al. *Animal Genetics* 19: 203-212, (1989)].

Hal has been shown to be the gene responsible for both porcine stress syndrome (PSS) and pale, soft exudative pork (PSEP) which result in unfavorable meat quality due to myolactosis in the immediate one to two hours post-slaughter. This represents a considerable economic problem in North America and Europe, with estimated annual losses of 300 million dollars in the United States alone [Harrision, G. G., "Porcine Malignant Hyperthermia, the Saga of the Hot Pig", in Britt, B. A., Ed. *Malignant Hyperthermia,* Boston, Martinus Nijhoff, 103-136, (1987)]. A DNA diagnostic test would provide a cheap and reliable means of determining MH status particularly in breeding programs and should assist in the design of breeding programs which aim to lose the Hal trait while maintaining beneficial characteristics. The RFLP analysis in pigs would be able to eliminate the Hal gene from several strains resulting in considerable saving in the industry.

The human cDNA clones as disclosed herein may be used to isolate pig cDNA clones from both homozygous normal and homozygous affected pigs. The sequence of the two genes can then be compared to determine the mutation in each strain. Once these are identified, tests similar to those outlined above can be developed to test the authenticity of and/or diagnose the porcine mutations. Knowledge of these mutations will allow for the identification of affected and heterozygous pigs without resorting to RFLP analysis and will extend the utility of the detection method to include the identification of affected pigs in herds in which the gene frequency is rare.

It is also feasible to develop polyclonal or monoclonal antibodies against specific peptide sequences that can be used to detect differences in normal and mutant ryanodine receptor proteins. It is likely that MH individuals (either human or porcine) have a section of the protein sequence either missing or altered. It is possible to use a specific segment of peptide sequence to make fusion protein antigens and or synthetic peptide antigens and raise antibodies to the specific segment. Thus, antibodies raised to the altered sequence (Mutant MH) should show positive immunostaining on muscle sections in human MH individuals, MH pigs, and heterozygous pigs, as they will react with antigen in the muscle. No staining should be observed in normal human or porcine individuals. Heterozygous pigs should be distinguishable from honozygous affected pigs by the use of antibody raised to the normal peptide. Similarly, these reactions could be observed with the more sensitive technique of Western blotting of extracts of muscle protein.

The DNA sequence disclosed herein can be manipulated in order to achieve expression and production of large quantitites of the protein for functional analysis and antibody production. Partial or full length cDNA sequences, which encode for HRR may be ligated to bacterial expression vectors (for example, pRIT, pGEX, or pATH). The DNA can also be transferred from its existing context to other cloning vehicles, such as other plasmids, bacteriophages, cosmids, animal virus, yeast artificial chromosomes, somatic cells, and other simple or complex organisms, such as bacteria, fungi, invertebrates, or plants. The cDNA sequence (or portions thereof) or a mini gene can be introduced into eukaryotic expression vectors by standard techniques. The expression vectors can also be introduced into recipient cells by conventional techniques, including transfection, calcium or strontium phosphate precipitation, electropotation, microinjection, protoplast fusion, or virus vectors.

Antibodies to various epitopes of the HRR protein can be raised to provide extensive information on the characteristics of the protein and other valuable information which can be used in immunoassays. The antibodies may be raised to fusion proteins containing defined portions of the HRR polypeptide or may be raised to protein fragments which are prepared by chemical synthesis. As already noted, fusion proteins may be developed by expression of vectors in suitable hosts. As to the chemical synthesis of the proteins, this is well within the skill of those knowledgeable in the art.

With the purified protein, which may be a developed by affinity chromatography, the protein fragments are coupled to a suitable carrier protein and injected into rabbits. Sera from the rabbits immunized with the protein fragments is screened in accordance with standard techniques to raise polyclonal antibodies. In accordance with well understood techniques, monoclonal antibodies may also be raised in accordance with the methodology of Kohlar and Millstein [Nature, 256:495 (1975)]. Mice are immunized with the selected protein as conjugated with suitable carrier. Hybridomas are developed and screened to select the desired monoclonal antibody. The antibodies, either poly or mono, are used in diagnostic determinations to detect the presence of certain epitopes of protein.

DNA sequences may also be subjected to site directed mutagenesis for comparitive function expression studies. If the nature of the human and pig mutations are very different, as is suggested by the different modes of inheritance of MH in humans (dominant) and pig (codominant), it may be desirable to create animal models which more closely resemble each human mutation. This could be achieved by site directed mutagenesis in conjunction with homologous recombination in embryonic stem cells, or by use of retrovirus vectors to create transgenic animals.

EXAMPLE 1

The $Ca2+$ release channel complex of rabbit skeletal muscle was isolated from heavy sarcoplasmic reticulum membranes enriched in [3H]ryanodine binding and $45Ca2+$ release activity by solubilization in CHAPS, followed by density gradient centrifugation through 5–20% sucrose (Lai et al., supra). The [3H]ryanodine receptor peak was collected, concentrated and recentrifuged. SDS polyacrylamide gel analysis of the pooled [3H]ryanodine receptor peak on a linear 5–12% polyacrylamide gradient gel revealed a single major high molecular weight band with an apparent relative molecular mass of approximately 400,000 daltons (Lai et al., supra). Therefore, in accordance with this technique, the ryanodine receptor protein was isolated and purified.

Hydrophilic tryptic peptides from the purified ryanodine receptor were separated by reverse phase-HPLC and subjected to automated NH2-terminal analysis by Edman degradation in an Applied Biosystems 470 gas phase sequenator with an on-line HPLC system for phenylthiohydantoin derivative analysis.

EXAMPLE 2

The λgt11 cDNA expression library, constructed from poly(A)+RNA from rabbit fast-twitch psoas muscle as described in Ellis, S. B. et al., Science 241: 1661–1664, (1988). It is understood by those skilled in the art that any library prepared from skeletal muscle according to established methods should be representative of the RNA species present in the tissue, and can therefore be the source of the clone to be isolated. The library was screened with an affinity-purified polyclonal antibody (Zorzato et al., supra) specific for the $Ca2+$ release channel. Screening of the library was carried out by the method of Young and Davis, Proc. Nat. Acad. Sci. U.S.A. 80: 1194–1198, (1983).

The screening of $3 \times 10^6$ recombinant clones led to the isolation of two cDNA clones in the region defined by nucleotide 14280–14629 and 13434–13758 in FIG. 2. Analysis of the sequences of these clones showed that both were rearranged when compared to the linear sequence of the human cDNA. Accordingly, restriction endonuclease fragments from these isolated cDNA clones were used as probes to isolate longer, unrearranged cDNA clones from the neonatal rabbit skeletal muscle cDNA library previously described by Mac-Lennan et al., supra. The longest clone obtained was 6.8 kb and it is defined by nucleotide 8615-15241 in FIGS. 2A to 2A-12. This clone was subcloned into the Bluescript ® (Stratagens) plasmid vector and sequenced.

The clone was extended by construction of a primer extension library using 100 ug of neonatal rabbit muscle poly(A)+RNA. The primer site was defined with 0.25 nmol of an 18mer oligonucleotide complementary to the rabbit equivalent of nucleotides 9118 to 9135 in FIGS. 2A to 2A-12. Primer extension was carried out using the Bethesda Research Laboratories cDNA synthesis kit. In vitro packaging was performed with 1-2 ul aliquots of each ligation mixture using the Gigapack Gold packaging extract. Subsequent screening was carried out with the unamplified library. In the first primer extension, the cDNA was extended up to nucleotide 4527. In the second extension, an 18mer oligonucleotide complementary to the rabbit equivalent of residues 4892 to 4909 in FIGS. 2A to 2A-12 was used to extend the cDNA to nucleotide 3231. In the third and final primer extension, an 18mer oligonucleotide complementary to the rabbit equivalent of residues 3499 to 3516 in FIGS. 2A to 2A-12 was used to extend the sequence into the 5' untranslated region of the mRNA.

EXAMPLE 3

Rabbit ryanodine receptor cDNA probes were used to screen a human skeletal muscle cDNA library in λgt10, described in Koenig, M. et al., Cell, 50: 509-517, (1987). In the first screen, over 30 clones were isolated but only one, of about 2000 bp (clone 2 in FIG. 1), had an internal EcoR1 restriction site. All others terminated at an EcoR1 restriction site 1641 bp upstream of the poly(A) site (FIG. 2), suggesting that the cDNA used to make the library was undermethylated, allowing the full length cDNA to be cleaved at EcoR1 sites prior to its ligation into the λgt10 vector. Accordingly, it was necessary to isolate rabbit cDNA clones first and then to use them as probes to identify and isolate new human cDNA clones. Eventually, a series of 6 linear cDNA clones were isolated from the library using rabbit cDNA probes (FIG. 1). As a further complication in the isolation of human cDNA clones, an adenine rich region between residues 8501 and 8512 in FIG. 2 acted as a second priming site for cDNA synthesis. While this led to the synthesis of an enhanced number of clones upstream of this site, it also terminated transcription. Thus clones 4 and 5 in FIG. 1 were separated, not by an EcoR1 cleavage site, but by an actual gap in the cDNA. Clone 6 was the last cDNA clone isolated from the library and it represented the 5' end of cDNAs primed at the internal Poly(A) site. The final clone, clone 7, was obtained from a primer extension library constructed from human skeletal muscle mRNA using the protocols that were used for primer extension of rabbit skeletal muscle mRNA. In this case the primer was a 17mer oligonucleotide complementary to residues 2620 to 2636 in FIGS. 2A to 2A-12. Genomic DNA encoding sequences overlapping the various EcoR1 restriction sites and the gap in the cDNA introduced by the second primer initiating site were isolated from a chromosome 19-specific library under the designation Lawrence Livermore LL19NL01 Human Chromosome 19 library in Charon 4A by the American Type Culture Collection, Rockville, Md.

Muscle was clamped, carefully dissected and transported to the laboratory in carbogenated Krebs Ringer solution maintained at 22° C. and pH 7.4. Also in carbogenated Krebs Ringer solution, biopsies were trimmed free of fat and divided into strips of one to five mm by 10 to 20 mm of approximately 100 to 300 mg. Only intact muscle strips were used. Muscle strips were secured at one end by a silk suture to a plastic electrode frame and placed in a 40 ml bathing chamber containing Krebs Ringer solution at 37° C. and pH 7.4 and aerated with 95% $O_2$, 5% $CO_2$ at 20 ml per minute. The muscle strip was then secured at the other end to a force displacement transducer which was coupled to a polygraph used to record the muscle tension.

Although preferred embodiments of the invention have been described herein in detail, it will be understood by those skilled in the art that variations may be made thereto without departing from the spirit of the invention or the scope of the appended claims.

We claim:

1. Isolated DNA encoding for human ryanodine receptor, comprising said DNA having the following characteristics;
    i) said DNA encoding for a protein having 5032 amino acids and a molecular weight of approximately 563,000 daltons, wherein said protein has the amino acid sequence of FIGS. 2A to 2A-12;
    ii) said DNA having length of approximately 15.3 kb;
    iii) said DNA being isolated from chromosome 19 of humans; and
    iv) said DNA having the restriction map of FIG. 1.

2. Isolated cDNA comprising the sequence encoding for amino acid positions 1 to 5032 of FIGS. 2A to 2A-12.

3. A DNA probe comprising one or more DNA fragments selected from the group of DNA fragments consisting of:
    i) HRR-1 of approximately 1.6 kb spanning nucleotides 13602 to 15243 of FIGS. 2A to 2A-12;
    ii) HRR-2 of approximately 2 kb spanning nucleotides 11613 to 13607 in FIGS. 2A to 2A-12;
    iii) HRR-3 of approximately 3.1 kb spanning nucleotides 8515 to 11618 of FIGS. 2A to 2A-12;
    iv) HRR-3-1000 of approximately 1 kb spanning nucleotides 8515 to 9554 of FIGS. 2A to 2A-12;
    v) HRR-3-1200 of approximately 1.2 kb spanning nucleotides 9549 to 10851 of FIGS. 2A to 2A-12;
    vi) HRR-4 of approximately 2.4 kb spanning nucleotides 6125 to 8493 of FIGS. 2A to 2A-12;
    vii) HRR-5 of approximately 3.8 kb spanning nucleotides 2391 to 6135 of FIGS. 2A to 2A-12;
    viii) and HRR-7A of approximately 2.2 kb spanning nucleotides 186 to 2396 of FIGS. 2A to 2A-12;
    ix) HRR-7B of approximately 0.4 kb spanning nucleotides 104 to 549 of FIGS. 2A to 2A-12.

4. A diagnostic DNA assay for determining susceptibility of a person to malignant hyperthermia where said person is from a family of one or more individuals who is susceptible to malignant hyperthermia, said assay comprising the steps of:
    i) isolating DNA from at least chromosome 19 of a person being tested;
    ii) performing RFLP analysis on said isolated chromosome 19 DNA and using said DNA probes of claim 3 as RFLP markers in said RFLP analysis;
    iii) detecting linkage with RFLP analysis of an affected family individual to determine if said person is susceptible to malignant hyperthermia.

* * * * *

UNITED STATES PATENT AND TRADEMARK OFFICE
CERTIFICATE OF CORRECTION

PATENT NO. : 5,413,907　　　　　　　　　　　　　　Page 1 of 2
DATED : May 9, 1995
INVENTOR(S) : Worton, et al It is certified that error appears in the above-indentified patent and that said Letters Patent is hereby corrected as shown below:

On the title page:

Other Publications, column 2, line 14, "Rosenger" should read —Rosenberg—.

Column 1, line 7, "(MH)" should read —MH—.
Column 4, line 29, "is" should read —are—.
Column 4, line 36, before "gene" insert —HRR—.
Column 4, line 42, "is a" should read —are—.
Column 4, line 43, "analysis" should read —analyses—.
Column 4, line 63, "(HER)" should read —(HRR)—.
Column 5, line 1, after "gene" insert —which—.
Column 5, line 20, "society" should be —Society—.
Column 6, line 36, after "clone" omit the period (.)
Column 8, line 47, "Genomis" should read —Genomics—.
Column 8, line 48, after "Sci" omit the comma (,).
Column 9, line 7, "HER" should read —HRR—.
Column 10, line 18, "is" should read —i.e.—.
Column 10, line 47, "cumulativele" should read —cumulatively—.
Column 11, line 30, "5a and 5b" should read —5A and 5B—.
Column 11, line 36, "PRESYM." should read —PRESUM.—.
Column 11, line 37, "5a" should read —5A—.
Column 11, line 65, "5b" should read —5B—.
Column 11, line 68, "5a" should read —5A—.
Column 12, line 13, "Similar" should read —similar—.
Column 14, line 10, "proc," should read —proc.—.

UNITED STATES PATENT AND TRADEMARK OFFICE
CERTIFICATE OF CORRECTION

PATENT NO. : 5,413,907
DATED : May 9, 1995
INVENTOR(S) : Worton et al.

It is certified that error appears in the above-indentified patent and that said Letters Patent is hereby corrected as shown below:

Column 15 line 24, "and or" should be --and/or--;
line 32, "honozygous" should be --homozygous--.

Column 16 line 15, "comparitive" should be --comparative--.

Column 18 before line 1, insert the heading --EXAMPLE 4--;
line 51, omit "and";
line 52, at the end of the line insert --and--.

Signed and Sealed this

Fifth Day of September, 1995

BRUCE LEHMAN

Attest:

Attesting Officer

Commissioner of Patents and Trademarks